(12) United States Patent
Jackson et al.

(10) Patent No.: US 8,377,055 B2
(45) Date of Patent: Feb. 19, 2013

(54) METHODS AND SYSTEMS FOR DETERMINING PHYSIOLOGIC CHARACTERISTICS FOR TREATMENT OF THE ESOPHAGUS

(75) Inventors: Jerome Jackson, Los Altos, CA (US);
Roger A. Stern, Cupertino, CA (US);
David S. Utley, Redwood City, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/189,793

(22) Filed: Jul. 25, 2011

(65) Prior Publication Data

US 2012/0004654 A1  Jan. 5, 2012

Related U.S. Application Data

(60) Continuation of application No. 12/787,324, filed on May 25, 2010, now Pat. No. 8,012,149, which is a continuation of application No. 11/244,385, filed on Oct. 4, 2005, now abandoned, which is a continuation-in-part of application No. 10/754,452, (Continued)

(51) Int. Cl.
*A61B 18/12* (2006.01)
*A61B 18/10* (2006.01)

(52) U.S. Cl. .......................... 606/34; 606/32
(58) Field of Classification Search ............... 606/32–50
See application file for complete search history.

(56) References Cited

U.S. PATENT DOCUMENTS

| | | |
|---|---|---|
| 552,832 A | 1/1896 | Fort |
| 1,798,902 A | 11/1928 | Raney |
| 3,517,128 A | 2/1968 | Hines |
| 3,901,241 A | 8/1975 | Allen, Jr. |
| 3,924,628 A | 12/1975 | Droegemueller et al. |
| 4,011,872 A | 3/1977 | Komiya |
| 4,196,724 A | 4/1980 | Wirt et al. |
| 4,304,239 A | 12/1981 | Perlin |
| 4,311,154 A | 1/1982 | Sterzer et al. |
| 4,407,298 A | 10/1983 | Lentz et al. |
| 4,411,266 A | 10/1983 | Cosman |
| 4,423,812 A | 1/1984 | Sato |

(Continued)

FOREIGN PATENT DOCUMENTS

| | | |
|---|---|---|
| DE | 3838840 | 5/1990 |
| DE | 4303882 | 8/1994 |

(Continued)

OTHER PUBLICATIONS

Castell, D.O. Gastroesophageal Reflux Disease: Current Strategies for Patient Management. Arch Fam Med. 1996; 5(4):221-227.

(Continued)

*Primary Examiner* — Michael Peffley
*Assistant Examiner* — Ronald Hupczey, Jr.
(74) *Attorney, Agent, or Firm* — Holland & Hart LLP

(57) ABSTRACT

A method and apparatus for treating abnormal mucosa in the esophagus is disclosed, such that the depth of the treated tissue is controlled. The depth of ablation is controlled by monitoring the tissue impedance and/or the tissue temperature. A desired ablation depth is also achieved by controlling the energy density or power density, and the amount of time required for energy delivery. A method and apparatus is disclosed for measuring an inner diameter of a body lumen, where a balloon is inflated inside the body lumen at a fixed pressure.

10 Claims, 13 Drawing Sheets

Related U.S. Application Data filed on Jan. 9, 2004, now abandoned, which is a continuation-in-part of application No. 10/370,645, filed on Feb. 19, 2003, now Pat. No. 7,530,979, which is a division of application No. 09/714,344, filed on Nov. 16, 2000, now Pat. No. 6,551,310.

(60) Provisional application No. 60/165,687, filed on Nov. 16, 1999.

(56) References Cited

U.S. PATENT DOCUMENTS

| | | | |
|---|---|---|---|
| 4,532,924 A | 8/1985 | Auth et al. | |
| 4,565,200 A | 1/1986 | Cosman | |
| 4,640,298 A | 2/1987 | Pless et al. | |
| 4,658,836 A | 4/1987 | Turner | |
| 4,662,383 A | 5/1987 | Sogawa et al. | |
| 4,674,481 A | 6/1987 | Boddie, Jr. et al. | |
| 4,676,258 A | 6/1987 | Inokuchi et al. | |
| 4,705,041 A | 11/1987 | Kim | |
| 4,709,698 A | 12/1987 | Johnston et al. | |
| 4,740,207 A | 4/1988 | Kreamer | |
| 4,765,331 A | 8/1988 | Petruzzi et al. | |
| 4,776,349 A | 10/1988 | Nashef et al. | |
| 4,860,744 A | 8/1989 | Johnson et al. | |
| 4,887,614 A | 12/1989 | Shirakami et al. | |
| 4,895,138 A | 1/1990 | Yabe | |
| 4,901,737 A | 2/1990 | Toone | |
| 4,906,203 A | 3/1990 | Margrave et al. | |
| 4,907,589 A | 3/1990 | Cosman | |
| 4,930,521 A | 6/1990 | Metzger et al. | |
| 4,943,290 A | 7/1990 | Rexroth et al. | |
| 4,947,842 A | 8/1990 | Marchosky et al. | |
| 4,949,147 A | 8/1990 | Bacuvier | |
| 4,955,377 A | 9/1990 | Lennox et al. | |
| 4,966,597 A | 10/1990 | Cosman | |
| 4,969,890 A | 11/1990 | Sugita et al. | |
| 4,976,711 A | 12/1990 | Parins et al. | |
| 4,979,948 A | 12/1990 | Geddes et al. | |
| 4,998,539 A | 3/1991 | Delsanti | |
| 5,006,119 A | 4/1991 | Acker et al. | |
| 5,010,895 A | 4/1991 | Maurer et al. | |
| 5,019,075 A | 5/1991 | Spears et al. | |
| 5,035,696 A | 7/1991 | Rydell | |
| 5,045,056 A | 9/1991 | Behl | |
| 5,046,512 A | 9/1991 | Murchie | |
| 5,047,028 A | 9/1991 | Qian | |
| 5,056,532 A | 10/1991 | Hull et al. | |
| 5,057,107 A | 10/1991 | Parins et al. | |
| 5,078,717 A | 1/1992 | Parins et al. | |
| 5,083,565 A | 1/1992 | Parins | |
| 5,084,044 A | 1/1992 | Quint | |
| 5,088,979 A | 2/1992 | Filipi et al. | |
| 5,094,233 A | 3/1992 | Brennan | |
| 5,100,423 A | 3/1992 | Fearnot | |
| 5,106,360 A | 4/1992 | Ishiwara et al. | |
| 5,117,828 A | 6/1992 | Metzger et al. | |
| 5,122,137 A | 6/1992 | Lennox | |
| 5,125,928 A | 6/1992 | Parins et al. | |
| 5,151,100 A | 9/1992 | Abele et al. | |
| 5,156,151 A | 10/1992 | Imran | |
| 5,163,938 A | 11/1992 | Kambara et al. | |
| 5,171,299 A * | 12/1992 | Heitzmann et al. | 604/100.03 |
| 5,190,541 A | 3/1993 | Abele et al. | |
| 5,192,297 A | 3/1993 | Hull | |
| 5,197,963 A | 3/1993 | Parins | |
| 5,197,964 A | 3/1993 | Parins | |
| 5,205,287 A | 4/1993 | Erbel et al. | |
| 5,215,103 A | 6/1993 | Desai | |
| 5,232,444 A | 8/1993 | Just et al. | |
| 5,236,413 A | 8/1993 | Feiring | |
| 5,242,441 A | 9/1993 | Avitall | |
| 5,254,126 A | 10/1993 | Filipi et al. | |
| 5,255,679 A * | 10/1993 | Imran | 600/375 |
| 5,256,138 A | 10/1993 | Vurek et al. | |
| 5,257,451 A | 11/1993 | Edwards et al. | |
| 5,263,493 A | 11/1993 | Avitall | |
| 5,275,162 A | 1/1994 | Edwards et al. | |
| 5,275,169 A * | 1/1994 | Afromowitz et al. | 600/486 |
| 5,275,608 A | 1/1994 | Forman et al. | |
| 5,275,610 A | 1/1994 | Eberbach | |
| 5,277,201 A | 1/1994 | Stern | |
| 5,281,216 A | 1/1994 | Klicek | |
| 5,281,217 A | 1/1994 | Edwards et al. | |
| 5,281,218 A | 1/1994 | Imran | |
| 5,290,286 A | 3/1994 | Parins | |
| 5,292,321 A | 3/1994 | Lee | |
| 5,293,869 A | 3/1994 | Edwards et al. | |
| 5,305,696 A | 4/1994 | Mendenhall | |
| 5,309,910 A | 5/1994 | Edwards et al. | |
| 5,313,943 A | 5/1994 | Houser et al. | |
| 5,314,438 A | 5/1994 | Shturman | |
| 5,314,466 A | 5/1994 | Stern et al. | |
| 5,316,020 A | 5/1994 | Truffer | |
| 5,324,284 A | 6/1994 | Imran | |
| 5,328,467 A | 7/1994 | Edwards et al. | |
| 5,334,196 A | 8/1994 | Scott et al. | |
| 5,336,222 A | 8/1994 | Durgin, Jr. et al. | |
| 5,345,936 A | 9/1994 | Pomeranz et al. | |
| 5,348,554 A | 9/1994 | Imran et al. | |
| 5,363,861 A | 11/1994 | Edwards et al. | |
| 5,365,926 A | 11/1994 | Desai | |
| 5,365,945 A | 11/1994 | Halstrom | |
| 5,366,490 A | 11/1994 | Edwards et al. | |
| 5,368,557 A | 11/1994 | Nita et al. | |
| 5,368,592 A | 11/1994 | Stern et al. | |
| 5,370,675 A | 12/1994 | Edwards et al. | |
| 5,370,678 A | 12/1994 | Edwards et al. | |
| 5,375,594 A | 12/1994 | Cueva | |
| 5,383,874 A | 1/1995 | Jackson et al. | |
| 5,383,876 A | 1/1995 | Nardella | |
| 5,383,917 A | 1/1995 | Desai et al. | |
| 5,385,544 A | 1/1995 | Edwards et al. | |
| 5,397,339 A | 3/1995 | Desai | |
| 5,398,683 A | 3/1995 | Edwards et al. | |
| 5,401,272 A | 3/1995 | Perkins | |
| 5,403,311 A | 4/1995 | Abele et al. | |
| 5,409,453 A | 4/1995 | Lundquist et al. | |
| 5,409,483 A | 4/1995 | Campbell et al. | |
| 5,411,025 A | 5/1995 | Webster, Jr. | |
| 5,413,573 A | 5/1995 | Koivukangas | |
| 5,415,657 A | 5/1995 | Taymor-Luia | |
| 5,416,020 A | 5/1995 | Severson et al. | |
| 5,421,819 A | 6/1995 | Edwards et al. | |
| 5,423,808 A | 6/1995 | Edwards et al. | |
| 5,423,811 A | 6/1995 | Imran et al. | |
| 5,423,812 A | 6/1995 | Ellman et al. | |
| 5,425,704 A | 6/1995 | Sakurai et al. | |
| 5,428,658 A | 6/1995 | Oettinger et al. | |
| 5,433,739 A | 7/1995 | Sluijter et al. | |
| 5,435,805 A | 7/1995 | Edwards | |
| 5,441,499 A | 8/1995 | Fritzsch | |
| 5,443,470 A | 8/1995 | Stern et al. | |
| 5,454,782 A | 10/1995 | Perkins | |
| 5,454,809 A | 10/1995 | Janssen | |
| 5,456,662 A | 10/1995 | Edwards et al. | |
| 5,456,682 A | 10/1995 | Edwards et al. | |
| 5,458,571 A | 10/1995 | Lampropoulos et al. | |
| 5,458,596 A | 10/1995 | Lax et al. | |
| 5,458,597 A | 10/1995 | Edwards et al. | |
| 5,462,545 A | 10/1995 | Wang et al. | |
| 5,465,717 A | 11/1995 | Imran et al. | |
| 5,470,308 A | 11/1995 | Edwards et al. | |
| 5,471,982 A | 12/1995 | Edwards et al. | |
| 5,472,441 A | 12/1995 | Edwards et al. | |
| 5,484,400 A | 1/1996 | Edwards et al. | |
| 5,486,161 A | 1/1996 | Lax et al. | |
| 5,490,984 A | 2/1996 | Freed | |
| 5,496,271 A | 3/1996 | Burton et al. | |
| 5,496,311 A * | 3/1996 | Abele et al. | 606/28 |
| 5,500,012 A | 3/1996 | Brucker et al. | |
| 5,505,728 A | 4/1996 | Ellman et al. | |
| 5,505,730 A | 4/1996 | Edwards | |
| 5,507,743 A | 4/1996 | Edwards et al. | |

| | | | | | | |
|---|---|---|---|---|---|---|
| 5,509,419 A | 4/1996 | Edwards et al. | | 5,904,711 A | 5/1999 | Flom et al. |
| 5,514,130 A | 5/1996 | Baker | | 5,925,044 A | 7/1999 | Hofmann et al. |
| 5,514,131 A | 5/1996 | Edwards et al. | | 5,938,694 A | 8/1999 | Jaraczewski et al. |
| 5,517,989 A | 5/1996 | Frisbie et al. | | 5,964,755 A | 10/1999 | Edwards |
| 5,520,684 A | 5/1996 | Imran | | 5,976,129 A | 11/1999 | Desai |
| 5,522,815 A | 6/1996 | Burgin, Jr. et al. | | 5,984,861 A | 11/1999 | Crowley |
| 5,524,622 A | 6/1996 | Wilson | | 5,997,534 A | 12/1999 | Tu et al. |
| 5,531,676 A | 7/1996 | Edwards et al. | | 6,006,755 A | 12/1999 | Edwards |
| 5,531,677 A | 7/1996 | Lundquist et al. | | 6,010,511 A * | 1/2000 | Murphy .................... 606/108 |
| 5,533,958 A | 7/1996 | Wilk | | 6,012,457 A | 1/2000 | Lesh |
| 5,536,240 A | 7/1996 | Edwards et al. | | 6,016,437 A | 1/2000 | Tu et al. |
| 5,536,267 A | 7/1996 | Edwards et al. | | 6,023,638 A | 2/2000 | Swanson et al. |
| 5,540,655 A | 7/1996 | Edwards et al. | | 6,027,499 A | 2/2000 | Johnston et al. |
| 5,542,916 A | 8/1996 | Hirsch et al. | | 6,033,397 A | 3/2000 | Laufer et al. |
| 5,542,928 A | 8/1996 | Evans et al. | | 6,039,701 A | 3/2000 | Sliwa et al. |
| 5,549,644 A | 8/1996 | Lundquist et al. | | 6,041,260 A | 3/2000 | Stern et al. |
| 5,549,661 A | 8/1996 | Korkis et al. | | 6,044,846 A | 4/2000 | Edwards |
| RE35,330 E | 9/1996 | Malone et al. | | 6,053,172 A | 4/2000 | Hovda et al. |
| 5,554,110 A | 9/1996 | Edwards et al. | | 6,053,913 A | 4/2000 | Tu et al. |
| 5,556,377 A | 9/1996 | Rosen et al. | | 6,056,744 A | 5/2000 | Edwards |
| 5,558,672 A | 9/1996 | Edwards et al. | | 6,059,719 A | 5/2000 | Yamamoto et al. |
| 5,558,673 A | 9/1996 | Edwards et al. | | 6,068,629 A | 5/2000 | Haissaguerre et al. |
| 5,562,720 A | 10/1996 | Stern et al. | | 6,071,277 A | 6/2000 | Farley et al. |
| 5,566,221 A | 10/1996 | Smith et al. | | 6,073,052 A | 6/2000 | Zelickson et al. |
| 5,569,241 A | 10/1996 | Edwards | | 6,086,558 A | 7/2000 | Bower et al. |
| 5,571,116 A | 11/1996 | Bolanos et al. | | 6,091,993 A | 7/2000 | Bouchier et al. |
| 5,572,578 A | 11/1996 | Lin et al. | | 6,091,995 A | 7/2000 | Ingle et al. |
| 5,578,007 A | 11/1996 | Imran | | 6,092,528 A | 7/2000 | Edwards |
| 5,588,432 A | 12/1996 | Crowley | | 6,095,966 A | 8/2000 | Chornenky et al. |
| 5,588,960 A | 12/1996 | Edwards et al. | | 6,096,054 A | 8/2000 | Wyzgala et al. |
| 5,591,195 A | 1/1997 | Taheri et al. | | 6,102,908 A | 8/2000 | Tu et al. |
| 5,599,345 A | 2/1997 | Edwards et al. | | 6,112,123 A | 8/2000 | Kelleher et al. |
| 5,609,151 A | 3/1997 | Mulier et al. | | 6,120,434 A | 9/2000 | Kimura et al. |
| 5,620,480 A | 4/1997 | Rudie | | 6,123,703 A | 9/2000 | Tu et al. |
| 5,621,780 A | 4/1997 | Smith et al. | | 6,123,718 A | 9/2000 | Tu et al. |
| 5,624,439 A | 4/1997 | Edwards et al. | | 6,138,046 A | 10/2000 | Dalton |
| 5,651,780 A * | 7/1997 | Jackson et al. ............ 606/1 | | 6,142,994 A | 11/2000 | Swanson et al. |
| 5,651,788 A | 7/1997 | Fleischer et al. | | 6,146,149 A | 11/2000 | Daoud |
| 5,658,278 A | 8/1997 | Imran et al. | | 6,149,647 A | 11/2000 | Tu et al. |
| 5,672,153 A | 9/1997 | Lax et al. | | 6,162,237 A | 12/2000 | Chan |
| 5,676,674 A | 10/1997 | Bolanos et al. | | 6,179,836 B1 | 1/2001 | Eggers et al. |
| 5,688,266 A | 11/1997 | Edwards et al. | | 6,182,666 B1 | 2/2001 | Dobak, III |
| 5,688,490 A | 11/1997 | Tournier et al. | | 6,183,468 B1 * | 2/2001 | Swanson et al. ............ 606/40 |
| 5,702,438 A | 12/1997 | Avitall | | 6,197,022 B1 | 3/2001 | Baker |
| 5,709,224 A | 1/1998 | Behl et al. | | 6,237,355 B1 | 5/2001 | Li |
| 5,713,942 A | 2/1998 | Stern et al. | | 6,238,392 B1 | 5/2001 | Long |
| 5,716,410 A | 2/1998 | Wang et al. | | 6,245,065 B1 | 6/2001 | Panescu et al. |
| 5,720,293 A | 2/1998 | Quinn et al. | | 6,254,598 B1 | 7/2001 | Edwards et al. |
| 5,730,128 A | 3/1998 | Pomeranz et al. | | 6,254,599 B1 | 7/2001 | Lesh et al. |
| 5,732,698 A | 3/1998 | Swanson et al. | | 6,258,087 B1 | 7/2001 | Edwards et al. |
| 5,738,096 A | 4/1998 | Ben-Haim | | 6,258,118 B1 | 7/2001 | Baum et al. |
| 5,748,699 A | 5/1998 | Smith | | 6,273,886 B1 | 8/2001 | Edwards et al. |
| 5,769,846 A | 6/1998 | Edwards et al. | | 6,321,121 B1 | 11/2001 | Zelickson et al. |
| 5,769,880 A | 6/1998 | Truckai et al. | | 6,325,798 B1 | 12/2001 | Edwards et al. |
| 5,779,698 A | 7/1998 | Clayman et al. | | 6,325,800 B1 | 12/2001 | Durgin et al. |
| 5,797,835 A | 8/1998 | Green | | 6,338,726 B1 | 1/2002 | Edwards et al. |
| 5,797,903 A | 8/1998 | Swanson et al. | | 6,355,031 B1 | 3/2002 | Edwards et al. |
| 5,800,334 A | 9/1998 | Wilk | | 6,355,032 B1 | 3/2002 | Hovda et al. |
| 5,800,429 A | 9/1998 | Edwards | | 6,358,245 B1 | 3/2002 | Edwards et al. |
| 5,807,261 A | 9/1998 | Benaron et al. | | 6,363,937 B1 | 4/2002 | Hovda et al. |
| 5,820,629 A | 10/1998 | Cox | | 6,383,181 B1 | 5/2002 | Johnston et al. |
| 5,823,197 A | 10/1998 | Edwards | | 6,394,949 B1 | 5/2002 | Crowley et al. |
| 5,823,955 A | 10/1998 | Kuck et al. | | 6,402,744 B2 | 6/2002 | Edwards et al. |
| 5,827,273 A | 10/1998 | Edwards | | 6,405,732 B1 | 6/2002 | Edwards et al. |
| 5,830,129 A | 11/1998 | Baer et al. | | 6,409,723 B1 | 6/2002 | Edwards |
| 5,830,213 A | 11/1998 | Panescu et al. | | H2037 H | 7/2002 | Yates et al. |
| 5,833,688 A | 11/1998 | Sieben et al. | | 6,415,016 B1 | 7/2002 | Chornenky et al. |
| 5,836,874 A | 11/1998 | Swanson et al. | | 6,416,511 B1 | 7/2002 | Lesh et al. |
| 5,842,984 A | 12/1998 | Avitall | | 6,423,058 B1 | 7/2002 | Edwards et al. |
| 5,846,196 A | 12/1998 | Siekmeyer et al. | | 6,425,877 B1 | 7/2002 | Edwards |
| 5,860,974 A * | 1/1999 | Abele ......................... 606/41 | | 6,428,536 B2 | 8/2002 | Panescu et al. |
| 5,861,036 A | 1/1999 | Godin | | 6,432,104 B1 | 8/2002 | Durgin et al. |
| 5,863,291 A | 1/1999 | Schaer | | 6,440,128 B1 | 8/2002 | Edwards et al. |
| 5,871,483 A | 2/1999 | Jackson et al. | | 6,448,658 B2 | 9/2002 | Takata et al. |
| 5,876,340 A | 3/1999 | Tu et al. | | 6,451,014 B1 | 9/2002 | Wakikaido et al. |
| 5,888,743 A | 3/1999 | Das | | 6,454,790 B1 | 9/2002 | Neuberger et al. |
| 5,891,134 A | 4/1999 | Goble et al. | | 6,464,697 B1 | 10/2002 | Edwards et al. |
| 5,895,355 A | 4/1999 | Schaer | | 6,468,272 B1 | 10/2002 | Koblish et al. |
| 5,902,263 A | 5/1999 | Patterson et al. | | 6,514,246 B1 | 2/2003 | Swanson et al. |

| Patent/Pub No. | Date | Name |
|---|---|---|
| 6,514,249 B1 | 2/2003 | Maguire et al. |
| 6,535,768 B1 | 3/2003 | Baker et al. |
| 6,544,226 B1 | 4/2003 | Gaiser et al. |
| 6,547,776 B1 | 4/2003 | Gaiser et al. |
| 6,547,787 B1 | 4/2003 | Altman et al. |
| 6,551,302 B1* | 4/2003 | Rosinko et al. ............... 604/505 |
| 6,551,310 B1 | 4/2003 | Ganz et al. |
| 6,551,315 B2 | 4/2003 | Kortenbach et al. |
| 6,562,034 B2 | 5/2003 | Edwards et al. |
| 6,572,578 B1 | 6/2003 | Blanchard |
| 6,572,610 B2 | 6/2003 | Kovalcheck et al. |
| 6,572,639 B1 | 6/2003 | Ingle et al. |
| 6,575,966 B2 | 6/2003 | Lane et al. |
| 6,589,238 B2 | 7/2003 | Edwards et al. |
| 6,613,047 B2 | 9/2003 | Edwards |
| 6,641,581 B2 | 11/2003 | Muzzammel |
| 6,663,626 B2 | 12/2003 | Truckai et al. |
| 6,673,070 B2 | 1/2004 | Edwards et al. |
| 6,682,528 B2 | 1/2004 | Frazier et al. |
| 6,689,130 B2 | 2/2004 | Arail et al. |
| 6,695,764 B2 | 2/2004 | Silverman et al. |
| 6,712,074 B2 | 3/2004 | Edwards et al. |
| 6,712,814 B2 | 3/2004 | Edwards et al. |
| 6,712,815 B2 | 3/2004 | Sampson et al. |
| 6,740,082 B2 | 5/2004 | Shadduck |
| 6,749,607 B2 | 6/2004 | Edwards et al. |
| 6,752,806 B2 | 6/2004 | Durgin et al. |
| 6,800,083 B2 | 10/2004 | Hiblar et al. |
| 6,837,886 B2 | 1/2005 | Collins et al. |
| 6,846,312 B2 | 1/2005 | Edwards et al. |
| 6,860,878 B2 | 3/2005 | Brock |
| 6,866,663 B2 | 3/2005 | Edwards et al. |
| 6,872,206 B2* | 3/2005 | Edwards et al. ............... 606/41 |
| 6,917,834 B2 | 7/2005 | Koblish et al. |
| 6,918,906 B2 | 7/2005 | Long |
| 6,923,808 B2 | 8/2005 | Taimisto |
| 6,929,642 B2 | 8/2005 | Xiao et al. |
| 6,953,469 B2 | 10/2005 | Ryan |
| 6,964,661 B2 | 11/2005 | Rioux et al. |
| 6,971,395 B2 | 12/2005 | Edwards et al. |
| 6,974,456 B2 | 12/2005 | Edwards et al. |
| 6,994,704 B2 | 2/2006 | Qin et al. |
| 7,004,938 B2 | 2/2006 | Ormsby et al. |
| 7,048,734 B1 | 5/2006 | Fleischman et al. |
| 7,056,320 B2 | 6/2006 | Utley et al. |
| 7,083,620 B2 | 8/2006 | Jahns et al. |
| 7,089,063 B2 | 8/2006 | Lesh et al. |
| 7,122,031 B2 | 10/2006 | Edwards et al. |
| 7,125,407 B2 | 10/2006 | Edwards et al. |
| 7,150,745 B2 | 12/2006 | Stern et al. |
| 7,160,294 B2 | 1/2007 | Croft |
| 7,165,551 B2 | 1/2007 | Edwards et al. |
| 7,167,758 B2 | 1/2007 | Baker et al. |
| 7,179,257 B2 | 2/2007 | West et al. |
| 7,293,563 B2 | 11/2007 | Utley et al. |
| 7,326,207 B2 | 2/2008 | Edwards |
| 7,329,254 B2 | 2/2008 | West et al. |
| 7,344,535 B2 | 3/2008 | Stern et al. |
| 7,416,549 B2 | 8/2008 | Young et al. |
| 7,425,212 B1* | 9/2008 | Danek et al. ............... 606/47 |
| 7,507,234 B2 | 3/2009 | Utley et al. |
| 7,507,238 B2 | 3/2009 | Utley et al. |
| 7,507,239 B2 | 3/2009 | Shadduck |
| 7,530,979 B2 | 5/2009 | Ganz et al. |
| 7,556,628 B2 | 7/2009 | Utley et al. |
| 7,632,268 B2 | 12/2009 | Utley et al. |
| 7,727,191 B2 | 6/2010 | Mihalik et al. |
| 7,850,685 B2 | 12/2010 | Kunis et al. |
| 7,959,627 B2 | 6/2011 | Utley et al. |
| 7,993,336 B2 | 8/2011 | Jackson et al. |
| 7,997,278 B2 | 8/2011 | Utley et al. |
| 8,012,149 B2 | 9/2011 | Jackson et al. |
| 2001/0041887 A1 | 11/2001 | Crowley |
| 2001/0044625 A1 | 11/2001 | Hata et al. |
| 2001/0051802 A1 | 12/2001 | Woloszko et al. |
| 2002/0013581 A1 | 1/2002 | Edwards et al. |
| 2002/0087151 A1 | 7/2002 | Mody et al. |
| 2002/0111623 A1 | 8/2002 | Durgin et al. |
| 2002/0128650 A1 | 9/2002 | McClurken |
| 2002/0143325 A1 | 10/2002 | Sampson et al. |
| 2002/0147447 A1 | 10/2002 | Long |
| 2002/0156470 A1 | 10/2002 | Shadduck |
| 2002/0177847 A1 | 11/2002 | Long |
| 2002/0183739 A1 | 12/2002 | Long |
| 2003/0009165 A1 | 1/2003 | Edwards et al. |
| 2003/0014046 A1* | 1/2003 | Edwards et al. ............... 606/41 |
| 2003/0045869 A1 | 3/2003 | Ryan |
| 2003/0069572 A1 | 4/2003 | Wellman et al. |
| 2003/0093117 A1 | 5/2003 | Saadat |
| 2003/0109837 A1 | 6/2003 | McBride-Sakal |
| 2003/0153905 A1 | 8/2003 | Edwards et al. |
| 2003/0158550 A1 | 8/2003 | Ganz et al. |
| 2003/0181900 A1 | 9/2003 | Long |
| 2003/0181905 A1 | 9/2003 | Long |
| 2003/0191512 A1* | 10/2003 | Laufer et al. ............... 607/101 |
| 2003/0216727 A1 | 11/2003 | Long |
| 2004/0087936 A1 | 5/2004 | Stern et al. |
| 2004/0122452 A1 | 6/2004 | Deem et al. |
| 2004/0147916 A1 | 7/2004 | Baker |
| 2004/0153120 A1 | 8/2004 | Seifert et al. |
| 2004/0172016 A1 | 9/2004 | Bek et al. |
| 2004/0204708 A1 | 10/2004 | Edwards et al. |
| 2004/0215180 A1 | 10/2004 | Starkebaum et al. |
| 2004/0215235 A1 | 10/2004 | Jackson et al. |
| 2004/0215296 A1 | 10/2004 | Ganz et al. |
| 2004/0236316 A1 | 11/2004 | Danitz et al. |
| 2004/0243124 A1 | 12/2004 | Im et al. |
| 2005/0010162 A1 | 1/2005 | Utley et al. |
| 2005/0033271 A1 | 2/2005 | Qin et al. |
| 2005/0070978 A1 | 3/2005 | Bek et al. |
| 2005/0090817 A1 | 4/2005 | Phan |
| 2005/0096713 A1 | 5/2005 | Starkebaum et al. |
| 2005/0107829 A1 | 5/2005 | Edwards et al. |
| 2005/0143727 A1 | 6/2005 | Koblish et al. |
| 2005/0149013 A1 | 7/2005 | Lee |
| 2005/0154386 A1 | 7/2005 | West et al. |
| 2005/0159743 A1 | 7/2005 | Edwards et al. |
| 2005/0171524 A1 | 8/2005 | Stern et al. |
| 2005/0187546 A1 | 8/2005 | Bek et al. |
| 2005/0215983 A1 | 9/2005 | Brock |
| 2005/0245926 A1 | 11/2005 | Edwards et al. |
| 2005/0288664 A1 | 12/2005 | Ford et al. |
| 2006/0009758 A1 | 1/2006 | Edwards et al. |
| 2006/0015162 A1 | 1/2006 | Edward et al. |
| 2006/0020276 A1 | 1/2006 | Saadat et al. |
| 2006/0041256 A1 | 2/2006 | Edwards et al. |
| 2006/0069303 A1 | 3/2006 | Couvillon |
| 2006/0086363 A1 | 4/2006 | Qin et al. |
| 2006/0095032 A1 | 5/2006 | Jackson et al. |
| 2006/0259028 A1 | 11/2006 | Utley et al. |
| 2006/0259029 A1 | 11/2006 | Utley et al. |
| 2006/0259030 A1 | 11/2006 | Utley et al. |
| 2006/0282071 A1 | 12/2006 | Utley et al. |
| 2007/0066973 A1 | 3/2007 | Stern et al. |
| 2007/0100333 A1 | 5/2007 | Jackson et al. |
| 2007/0118104 A1 | 5/2007 | Wallace et al. |
| 2007/0118159 A1 | 5/2007 | Deem et al. |
| 2007/0167963 A1 | 7/2007 | Deem et al. |
| 2007/0219570 A1 | 9/2007 | Deem et al. |
| 2008/0097427 A1 | 4/2008 | Stern et al. |
| 2008/0275445 A1 | 11/2008 | Kelly et al. |
| 2008/0319350 A1 | 12/2008 | Wallace et al. |
| 2009/0012512 A1 | 1/2009 | Utley et al. |
| 2009/0012513 A1 | 1/2009 | Utley et al. |
| 2009/0012518 A1 | 1/2009 | Utley et al. |
| 2009/0036733 A1 | 2/2009 | Wallace et al. |
| 2009/0048593 A1 | 2/2009 | Ganz et al. |
| 2009/0336886 | 2/2009 | Utley et al. |
| 2009/0177194 A1 | 7/2009 | Wallace et al. |
| 2009/0187181 A1 | 7/2009 | Shadduck |
| 2009/0318914 A1 | 12/2009 | Utley et al. |
| 2010/0063495 A1 | 3/2010 | Edwards et al. |
| 2010/0191237 A1 | 7/2010 | Shadduck |

FOREIGN PATENT DOCUMENTS

| | | |
|---|---|---|
| EP | 0105677 A1 | 4/1984 |
| EP | 0115420 A2 | 8/1984 |
| EP | 0139607 B1 | 5/1985 |

| | | | |
|---|---|---|---|
| EP | 0251745 A1 | 1/1988 |
| EP | 0521595 A2 | 1/1993 |
| EP | 0608609 B1 | 8/1994 |
| EP | 1323382 A1 | 7/2003 |
| EP | 1634542 B1 | 3/2006 |
| JP | 05500179 A | 1/1993 |
| JP | 7-184919 | 7/1995 |
| JP | 8-506738 | 7/1996 |
| JP | 8-509875 | 10/1996 |
| JP | 2001037773 A | 2/2001 |
| JP | 2005503181 | 2/2005 |
| WO | WO 91/01773 A1 | 2/1991 |
| WO | WO 91/03207 A1 | 3/1991 |
| WO | WO 92/10142 A1 | 6/1992 |
| WO | WO 93/08755 A1 | 5/1993 |
| WO | WO 94/07446 A1 | 4/1994 |
| WO | WO 94/10925 A1 | 5/1994 |
| WO | 9421178 A1 | 9/1994 |
| WO | WO 94/21165 A1 | 9/1994 |
| WO | WO 94/22366 A1 | 10/1994 |
| WO | WO 94/26178 A1 | 11/1994 |
| WO | WO 95/18575 A1 | 7/1995 |
| WO | WO 95/19142 A1 | 7/1995 |
| WO | WO 95/25472 A1 | 9/1995 |
| WO | WO 96/00042 A1 | 1/1996 |
| WO | WO 96/16606 A1 | 6/1996 |
| WO | WO 96/29946 A1 | 10/1996 |
| WO | WO 97/04702 A1 | 2/1997 |
| WO | WO 97/06857 A2 | 2/1997 |
| WO | WO 97/32532 A1 | 9/1997 |
| WO | WO 97/43971 A1 | 11/1997 |
| WO | WO 98/12999 A2 | 4/1998 |
| WO | WO 98/14238 A1 | 4/1998 |
| WO | WO 98/18393 A1 | 5/1998 |
| WO | WO 99/03413 A1 | 1/1999 |
| WO | WO 99/35987 A1 | 7/1999 |
| WO | WO 99/42046 A1 | 8/1999 |
| WO | WO 99/55245 A1 | 11/1999 |
| WO | WO 00/01313 A1 | 1/2000 |
| WO | WO 00/59393 A1 | 10/2000 |
| WO | WO 00/62699 A2 | 10/2000 |
| WO | 0066052 A1 | 11/2000 |
| WO | WO 00/66017 A1 | 11/2000 |
| WO | WO 00/66021 A1 | 11/2000 |
| WO | WO 00/69376 A1 | 11/2000 |
| WO | WO 01/22897 A1 | 4/2001 |
| WO | WO 01/35846 A1 | 5/2001 |
| WO | WO 01/45550 A2 | 6/2001 |
| WO | WO 01/89440 A2 | 11/2001 |
| WO | WO 02/096327 A2 | 12/2002 |
| WO | WO 03/070091 A1 | 8/2003 |
| WO | WO 03/092609 A2 | 11/2003 |
| WO | 2004043280 A1 | 5/2004 |
| WO | WO 2007/001981 A2 | 1/2007 |
| WO | 2007044244 A2 | 4/2007 |
| WO | 2007061984 A2 | 5/2007 |

OTHER PUBLICATIONS

Dallamagne et al; Laparoscopic Nissen Fundoplication: Preliminary. Surgical Laparoscopy and Endoscopy. 1991; 1(3):138-143.

Hinder et al; The Technique of Laparoscopic Nissen Fundoplication. Surgical Laparoscopy and Endoscopy. 1992; 2(3):265-272.

Kaneko et al; Physiological Laryngeal Pacemaker. Trans Am Soc. Artif Intern Organs. 1985; XXXI:293-296.

Karlstrom et al; Ectopic Jejunal Pacemakers and Enterogastric Reflux Roux Gastrectomy: Effect of Intestinal Pacing. Surgery. 1989; 106(3):486-495.

Kelly, K.A. et al; Duodenal-Gastric Reflux and Slowed Gastric Emptying by Electrical Pacing of the Canine Duodenal Pacesetter Potential. Gastroenterology. 1977; 72(3):429-433.

Mugica, et al. Direct Diaphragm Stimulation. PACE. 1987; 10:252-256.

Mugica, et al., Preliminary Test of a Muscular Diaphragm Pacing System on Human Patients. Neurostimulation: An Overview, chapter 21. 1985; 263-279.

Reynolds, J.C. Influence of Pathophysiology, Severity, and Cost on the Medical Management of Gastroesophageal Reflux Disease. Am J. Health-Syst Phar. 1996; 53(22sul3):S5-S12.

Rice et al; Endoscopic Paranasal Sinus Surgery. Chapter 5, Functional Endoscopic Paranasal Sinus Surgery, The Technique of Messerklinger. Raven Press. 1988; 75-102.

Rice et al; Endoscopic Paranasal Sinus Surgery. Chapter 6, Total Endoscopic Sphenoethmoidectomy. The Technique of Wigand. Raven Press. 1988; 103-125.

Salameh et al; An Animal Model Study to Clarify and Investigate Endoscopic Tissue Coagulation by Using a New Monopolar Device. Gastrointestinal Endoscopy; 2004; 59 (1): 107-112.

Urshel, J.D. Complications of Antireflux Surgery. Am J. Surg. 1993; 166 (1):68-70.

Wallace et al.; U.S. Appl. No. 13/051,738 entitled "Selectively expandable operative element support structure and methods of use," filed Mar. 18, 2011.

Jackson, Jerome; U.S. Appl. No. 13/181,484 entitled "Methods and systems for treatment of tissue in a body lumen," filed Jul. 12, 2011.

Utley et al.; U.S. Appl. No. 13/181,490 entitled "Precision ablating method," filed Jul. 12, 2011.

* cited by examiner

Diameter Estimation Algorithm

| Object Diameter (mm) | Diameter Measuring Probe Inflation Volume (cm3) | ((f)v/6)+(L/4)*(f) | d^2 | d(cm) | Circular Diameter Calculation (mm) | Difference | Percent Error | Corrected Diameter Estimate (mm) (1.104 factor) |
|---|---|---|---|---|---|---|---|---|
| 20 cc syringe | 13 | 3.816930354 | 3.40586 | 1.845602162 | 18.45602 | | | |
| 19 mm tubing - 1 | 16.5 | 3.816930354 | 4.32235 | 2.079145364 | 20.79145 | 1.741454 | 9.141489 | 18.83283844 |
| 16 mm tubing | 11.5 | 3.816930354 | 3.01289 | 1.735756499 | 17.35768 | 1.482685 | 9.339748 | 15.72254075 |
| Pig Esophagus | 40 | 3.816930354 | 10.4796 | 3.237224942 | 32.37225 | -1.62775 | -4.7875 | 29.32268968 |
| 25 mm tubing | 32 | 3.816930354 | 8.3837 | 2.895462011 | 28.95462 | 3.55462 | 13.99457 | 28.22701097 |
| 19 mm tubing - 2 | 16.5 | 3.816930354 | 4.32283 | 2.079145364 | 20.79145 | 1.741454 | 9.141489 | 18.83283844 |

METHODS AND SYSTEMS FOR DETERMINING PHYSIOLOGIC CHARACTERISTICS FOR TREATMENT OF THE ESOPHAGUS

CROSS-REFERENCES TO RELATED APPLICATIONS

This application is a continuation of U.S. patent application Ser. No. 12/787,324 filed May 25, 2010, now U.S. Pat. No. 8,012,149, which is a continuation of U.S. patent application Ser. No. 11/244,385 filed Oct. 4, 2005, now abandoned, which is a continuation-in-part of U.S. patent application Ser. No. 10/754,452 flied Jan. 9, 2004, now abandoned, which is a continuation-in-part of U.S. patent application Ser. No. 10/370,645, filed Feb. 19, 2003, now U.S. Pat. No. 7,530,979, which is a divisional of Ser. No. 09/714,344 filed Nov. 16, 2000, now U.S. Pat. No. 6,551,310, which claims the benefit under 35 USC 119(e) of U.S. Provisional Application No. 60/165,687 filed Nov. 16, 1999, the full disclosure of which are fully incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

Field of the Invention

The present invention relates generally to medical methods and systems. More particularly, the invention is directed to methods and systems for treating and determining physiologic characteristics of body lumens such as the esophagus.

BACKGROUND

The human body has a number of internal body lumens or cavities located within, many of which have an inner lining or layer. These inner linings can be susceptible to disease. In some cases, surgical intervention can be required to remove the inner lining in order to prevent the spread of disease to otherwise healthy tissue located nearby.

Those with persistent problems or inappropriate relaxation of the lower esophageal sphincter can develop a condition known as gastro esophageal reflux disease, manifested by classic symptoms of heartburn and regurgitation of gastric and intestinal contents. The causative agent for such problems may vary. Patients with severe forms of gastroesophageal reflux disease, no matter what the cause, can sometimes develop secondary damage of the esophagus due to the interaction of gastric or intestinal contents with esophageal cells not designed to experience such interaction.

The esophagus is composed of three primary tissue layers; a superficial mucosal layer lined by squamous epithelial cells, a middle submucosal layer and a deeper muscle layer. When gastroesophageal reflux occurs, the superficial squamous epithelial cells are exposed to gastric acid, along with intestinal bile acids and enzymes. This exposure may be tolerated, but in some cases can lead to damage and alteration of the squamous cells, causing them to change into taller, specialized columnar epithelial cells. This metaplastic change of the mucosal epithelium from squamous cells to columnar cells is called Barrett's esophagus, named after the British surgeon who originally described the condition.

Barrett's esophagus has important clinical consequences, since the Barrett's columnar cells can, in some patients, become dysplastic and then progress to a certain type of deadly cancer of the esophagus. The presence of Barrett's esophagus is the main risk actor for the development of adenocarcinoma of the esophagus.

Accordingly, attention has been focused on identifying and removing this abnormal Barrett's columnar epithelium in order to mitigate more severe implications for the patient. Devices and methods for treating abnormal body tissue by application of various forms of energy to such tissue have been described, such as radio frequency ablation. However, without precise control of the depth of penetration of the energy means, these methods and devices are deficient. Uncontrolled energy application can penetrate too deeply into the esophageal wall, beyond the mucosa and submucosal layers, into the muscularis externa, potentially causing esophageal perforation, stricture or bleeding. Accordingly, proper administration of the correct amount of treatment energy to the tissue can be facilitated by knowledge of the size of the esophagus and area to be treated.

Additionally, medical procedures for treating Barrett's esophagus typically involve deployment of an expandable catheter inside the esophagus. Expandable catheters are preferred because the profile of the catheter is ideally as small as possible to allow for ease of delivery, while treatment of the esophagus is most efficiently performed when the catheter is at or slightly larger than the diameter of the esophageal wall. Proper sizing and/or pressurization of the delivery device is therefore desirable to prevent over-distension of the organ, which could result in harm to the organ, or under-expansion of the catheter, which often results in incomplete treatment. Accordingly, accurate and simple measurement of the size of the lumen and control of the pressure of the catheter on the lumen surface promotes the proper engagement and delivery of energy to the luminal wall so that a uniform and controlled depth of treatment can be administered. In addition to calculating luminal dimensions, the compliance of the lumen can be determined by measuring the cross section of the lumen at two or more pressure values.

Therefore, it would be advantageous to have methods and systems for accurately determining in vivo the size and optionally the compliance of a body lumen such as the esophagus. In addition, it would be desirable to provide a method and system for treating the body lumen once having determined its size. At least some of these objectives will be met by the present invention.

Description of the Background Art

U.S. Pat. No. 5,275,169 describes apparatus and methods for determining physiologic characteristics of blood vessels. The device measures the diameter and wall compliance of the blood vessel, and does not administer treatment. Additionally, the method relies on using only an incompressible fluid to inflate a balloon inside a blood vessel. Other patents of interest include U.S. Pat. Nos. 6,010,511; 6,039,701; and 6,551,310.

SUMMARY OF THE DISCLOSURE

The present invention comprises methods and systems for sizing a body lumen, such as the esophagus. Methods and systems are also provided for treating the body lumen once the proper measurements have been made.

Although the following description will focus on embodiments configured for treatment of the esophagus, other embodiments may be used to treat any other suitable lumen in the body. In particular, the methods and systems of the present invention may be used whenever accurate measurement of a body lumen or uniform delivery of energy is desired to treat a controlled depth of tissue in a lumen or cavity of the body, especially where such body structures may vary in size. Therefore, the following description is provided for exemplary purposes and should not be construed to limit the scope of the invention.

In general, in one aspect, the invention features a method for measuring an inner diameter of a body lumen including inserting a balloon in the body lumen; inflating the balloon inside the body lumen using an expansion medium; and monitoring a mass of the expansion medium inside the balloon.

Implementations of the invention can include one or more of the following features. Monitoring the mass of the expansion medium can be performed using a mass flow sensor. Additionally, the expansion medium can be a gas or a liquid. The balloon can be inflated at a fixed pressure, and the fixed pressure can be approximately 4 psig.

In general, in another aspect, the invention features a method for treating tissue in a body lumen including deploying a selected electrode structure at the surface of the tissue; delivering energy to the electrode structure to ablate the tissue to a depth from the surface; and controlling the depth of ablated tissue by monitoring a change in tissue impedance.

Controlling the depth of ablated tissue can include monitoring when the tissue impedance reaches a targeted impedance value. In one implementation, the targeted impedance value ranges from approximately 0.5 ohms to 10 ohms. In another implementation, controlling the depth of ablated tissue can additionally include monitoring when the tissue impedance changes a specified percentage from an initial tissue impedance level. In a further implementation, controlling the depth of ablated tissue can include monitoring when the tissue impedance reaches its minimum value. In a particular implementation, the desired depth of ablated tissue is approximately between 0.5 mm and 1 mm.

in general, in another aspect, the invention features a method for treating tissue of a body lumen, including: deploying an electrode structure at a surface of the tissue; delivering energy to the electrode structure to ablate the tissue to a depth from the surface; and controlling the depth of tissue ablation of the tissue by monitoring a change in the tissue temperature.

In one embodiment of this aspect of the invention, controlling the depth of tissue ablation includes monitoring when the tissue temperature reaches a target range. The temperature target range can be between approximately 65° and 95° C., and the energy can be delivered as long as the measured tissue temperature does not exceed a maximum temperature. In one implementation, the maximum temperature is approximately 95° C.

in general, in another aspect, the invention features a method for treating abnormal tissue inside a body lumen, including: automatically determining an inner diameter of the body lumen at a location proximal to the abnormal tissue; deploying an electrode structure at a surface of the tissue at the proximal location; and delivering energy to the electrode structure for treating the tissue.

In one embodiment of this aspect of the invention, the inner diameter of the body lumen can be determined by automatically inflating and deflating a balloon inside the body lumen using an expansion medium. This embodiment can further include monitoring a mass of the expansion medium inside the balloon and controlling a depth of treated tissue. In one implementation, controlling the depth of treated tissue includes controlling an amount of power delivered to the tissue over time. In other implementations, controlling the depth of treated tissue includes normalizing power delivered to the tissue over time; and/or controlling the depth of treated tissue by controlling an amount of energy delivered to the tissue over time; and/or controlling the depth of treated tissue by controlling delivered energy density; and/or controlling the depth of treated tissue by monitoring and controlling tissue impedance over time; and/or controlling the depth of treated tissue by monitoring and controlling tissue temperature over time.

Implementations of the invention can include one or more of the following features. Controlling an amount of power delivered to the tissue by rapidly increasing the power until it reaches a set target value and/or controlling the amount of power delivered by using a proportional integral derivative controller.

In general, in another aspect, the invention features an apparatus for treating a tissue inside a body lumen including: an electrode structure adapted to be positioned at a surface of the tissue inside the body lumen, wherein the electrode structure is coupled to an expansion member; and a generator for producing and delivering energy to the electrode structure; wherein the generator is adapted to automatically inflate the expansion member inside the body lumen and control the pressure inside the expansion member during treatment of the tissue.

Implementations of the invention can include one or more of the following features. The expansion member can be a balloon coupled to a catheter. The apparatus can further include a storage device for storing generator settings. In one implementation, the storage device is an EEPROM. The apparatus can further include a pump for automatically inflating and deflating the expansion member.

The generator of the apparatus can be adapted to determine an inner diameter of the body lumen using an inflatable balloon. In one implementation, the generator is adapted to control the amount of energy delivered to the tissue over time based on the measured diameter of the esophagus. In another implementation, the generator is adapted to normalize the density of energy delivered to the tissue based on the measured diameter of the esophagus. In yet another implementation, the generator is adapted to control the amount of power delivered to the tissue over time based on the measured diameter of the esophagus. In another implementation, the generator is adapted to control the energy delivered to the electrode structure. In another implementation, the generator is adapted to control the power delivered to the electrode structure. In yet another implementation, the generator is adapted to normalize the amount of power delivered to the tissue over time based on the measure diameter of the esophagus. In a further implementation the generator is adapted to detect whether a catheter is attached thereto and to identify a characteristic of the attached catheter. In a related implementation, the apparatus can further include a storage device adapted to store information about the attached catheter.

The apparatus can further include a footswitch coupled to the generator and adapted to control the energy delivered to the electrode structure and/or a display for displaying information to a user.

In another implementation, the generator is adapted to be manually controlled by a user such that the user controls the energy delivered to the electrode structure over time.

The apparatus can further include a proportional integral derivative controller adapted to gradually increase power delivered to the electrode structure until it reaches a set target value.

In general, in another aspect, the invention features an apparatus for treating a tissue inside a body lumen including: an electrode structure adapted to be positioned at a surface of the tissue inside the body lumen, wherein the electrode structure is coupled to an expansion member; and a generator for producing, delivering and controlling energy delivered to the electrode structure; wherein the generator is adapted to determine an inner diameter of the body lumen.

In one aspect of the invention, a method for treating a body lumen at a treatment location comprises measuring a luminal dimension at the treatment location of the lumen, selecting an electrode deployment device having an array of electrodes or other electrode structure with a pre-selected deployed size which corresponds to the measured dimension, positioning the electrode deployment device at the treatment location within the lumen, deploying the electrode array to the pre-selected deployed state to engage a wall of the lumen, and delivering energy to the electrodes for treatment of the luminal tissue.

In some embodiments, measuring the luminal dimension comprises positioning a sizing member at the treatment location within the lumen, expanding the sizing member until it engages an inside wall of the lumen, and calculating the luminal dimension at the treatment location of the esophagus based on the expansion of the sizing member. Often, expanding the sizing member comprises inflating a sizing balloon by introducing an expansion medium. The expansion medium may be a compressible or non-compressible fluid. In some embodiments, the lumen dimensions are calculated by determining the amount of the expansion medium introduced to the sizing balloon while it is inflated. For example, the mass or volume of the expansion medium can be measured by use of a mass-flow meter or the like. Optionally, a pressure sensor may be coupled to the sizing balloon, so that the luminal dimension can be calculated from the measured amount of expansion medium introduced to the balloon at a given pressure. Alternatively, the sizing member may comprise a basket, plurality of struts, or calipers, or the like. The lumen may also be measured by ultrasound, optical, or fluoroscopic imaging or by use of measuring strip.

In embodiments where a sizing balloon is employed, the sizing balloon may comprise any material or configuration. In general, the sizing balloon is cylindrical and has a known length and a diameter that is greater than the diameter of the target lumen. In this configuration, the sizing balloon is non-distensible, such as a bladder having a diameter in its fully expanded form that is larger than the lumen diameter. Suitable materials for the balloon may comprise a polymer such as polyimide or polyethylene terephthalate (PET). Alternatively, the balloon may comprise a mixture of polymers and elastomers.

Once the lumen dimensions are determined, an electrode deployment device matching the measured luminal dimension may be selected from an inventory of devices having different electrode deployment sizes. In some embodiments, the electrode deployment device is transesophageally delivered to a treatment area within the esophagus. For example, delivering the device may be facilitated by advancing a catheter through the esophagus, wherein the catheter carries the electrode array and an expansion member. The expansion member may comprise any of the materials or configurations of the sizing member, such as an inflatable cylindrical balloon comprising a polymer such as polyimide or PET.

In some aspects of the invention, the array of electrodes or other electrode structure is arranged on a surface of a dimensionally stable support such as a non-distensible, electrode backing. The backing may comprise a thin, rectangular sheet of polymer materials such as polyimide, polyester or other flexible thermoplastic or thermosetting polymer film, polymer covered materials, or other nonconductive materials. The backing may also comprise an electrically insulating polymer, with an electro-conductive material, such as copper, deposited onto a surface. For example, an electrode pattern can be etched into the material to create an array of electrodes. The electrode pattern may be aligned in an axial or traverse direction across the backing, formed in a linear or non-linear parallel array or series of bipolar pairs, or other suitable pattern. In many embodiments, delivering energy comprises applying radiofrequency (RF) energy to tissue of the body lumen, through the electrodes. Depending on the desired treatment effect, the electrodes may be arranged to control the depth and pattern of treatment. For treatment of esophageal tissue, the electrode widths are less than 3 mm, typically a width in the range from 0.1 mm to 3 mm, preferably 0.1 mm to 0.3 mm, and adjacent electrodes are spaced apart less than 3 mm, typically in the range from 0.1 mm to 3 mm, preferably from 0.1 mm to 0.3 mm. Alternatively, energy may be delivered by use of structures other than those having an array of electrodes. For example, the electrode structure may comprise a continuous electrode arranged in a helical pattern over the balloon.

In another method of the present invention, the measurement of the luminal dimension may be used to determine the amount of energy delivered to the tissue of the lumen. For example, a method for treating the tissue of a body lumen at a treatment location comprises measuring a luminal dimension at a location of the lumen, positioning an electrode deployment device at that location, deploying the expansion member to engage an electrode array to a wall of the lumen; and delivering sufficient energy to the electrode array for treatment of the luminal tissue based on the measured dimension of the lumen. In general, the amount of power delivered to the electrodes will vary depending on the type of treatment and the overall surface area of the luminal tissue to be treated. In some embodiments, the expansion member can variably expand to engage the wall of the lumen independent of the size of the lumen. For esophageal treatment, the expansion member may comprise a balloon that can expand to a range of diameters between 12 mm and 50 mm. Typically, the total energy density delivered to the esophageal tissue will be in the range from 1 $J/cm^2$ to 50 $J/cm^2$, usually being from 5 $J/cm^2$ to 15 $J/cm^2$. In order to effectively ablate the mucosal lining of the esophagus and allow re-growth of a normal mucosal lining without creating damage to underlying tissue structures, it is preferable to deliver the radiofrequency energy over a short time span in order to reduce the effects of thermal conduction of energy to deeper tissue layers, thereby creating a "searing" effect. It is preferable to deliver the radiofrequency energy within a time span of less than 5 seconds. An optimal time for effective treatment is less than 1 second, and preferably less than 0.5 second or 0.25 seconds. The lower bound on time may be limited by the ability of the RF power source to deliver high powers.

In one aspect of the invention, a method for measuring an internal dimension at a location in a body lumen comprises positioning a cylindrical balloon at a location within the lumen, inflating the balloon with an expansion medium to engage an inside wall of the lumen, monitoring the extent of engagement of the balloon, determining the amount of expansion medium in the balloon while inflated at the location, and calculating the internal dimension of the esophagus based on the length of the balloon and the measured amount of expansion medium inside the balloon. In some embodiments, the balloon is transesophageally delivered to a treatment area within the esophagus by advancing a catheter carrying the balloon through the esophagus. Often, the balloon is non-distensible and has a diameter that is greater than the diameter of the inside wall of the lumen. The balloon may be filled with an expansion medium that is a compressible fluid, such as air.

Monitoring the extent of engagement comprises determining the expansion of the balloon via a pressure sensor coupled to the balloon, wherein the extent of engagement is determined by the internal pressure exerted from the expansion medium as measured by the pressure sensor and by visual verification. The pressure sensor may comprise any device for determining the pressure inside a vessel, such as a strain gauge. Alternatively, the extent of engagement may be monitored by determining the expansion of the balloon via visual inspection. In some embodiments, the balloon may be expanded to apply pressure to the inside wall of the lumen, thereby causing the lumen to stretch.

In one aspect of the invention, a method for determining wall compliance of an esophagus comprises positioning a balloon at a location within the esophagus, inflating the balloon with a compressible fluid, measuring the static pressure within the balloon, measuring the total amount of fluid within the balloon at least two static pressure values, and calculating the wall compliance based on the variation in the amount of fluid between a first measured pressure and a second measured pressure. For esophageal treatment, the static pressure values to be used are typically below 10 psig, and preferably at or below 7 psig.

In another aspect, a system for treating tissue of a body lumen comprises a sizing member for measuring the cross section at a location of the lumen and a catheter having a set of individual treatment devices, each device comprising an electrode array adapted to treat a target location, wherein at least some of the arrays are adapted to treat locations having different sizes determined by the sizing member. In some embodiments, the sizing member comprises an inflatable, noncompliant sizing balloon that is oversized with respect to the inside wall of the lumen. The sizing balloon may be cylindrical with a diameter that is oversized with respect to the inside wall of the lumen. The sizing balloon may further be coupled to a pressure sensor for determining the internal pressure in the balloon from the introduction of the expansion medium. In addition, the system may further comprise a measuring means, such as a mass flow meter, for determining the amount of fluid in the sizing balloon.

In some embodiments, each of the individual treatment devices further include an expansion member comprising an inflatable balloon. Generally, each balloon is cylindrical and ranges in diameter from 12 mm to 50 mm when expanded. A balloon within the range is selected based on the measurement made from the sizing balloon so that when the balloon is expanded to its fully inflated shape, it properly engages the wall of the lumen. Typically, the expansion member is inflated with the same medium as the sizing balloon. Optionally, the treatment device may further include a pressure sensor as an extra precaution against over-distension of the organ.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

In various embodiments, the present invention provides methods and systems for measuring, and treating at a controlled and uniform depth, the inner lining of a lumen within a patient. It will be appreciated that the present invention is applicable to a variety of different tissue sites and organs, including but not limited to the esophagus. A treatment apparatus including a sizing member and a treatment device comprising an expandable electrode array is provided. The sizing member is first positioned at a treatment site within the lumen. Once in place, the sizing member is expanded to engage the wall of the lumen to obtain the dimensions of the lumen. The sizing member is removed, and at least a portion of the treatment device is positioned at the tissue site, where the electrode array is expanded to contact the tissue surface according to the measurements made by the sizing member.

Sufficient energy is then delivered from the electrode array to impart a desired therapeutic effect, such as cell necrosis, to a discrete layer of tissue.

Figure 1:
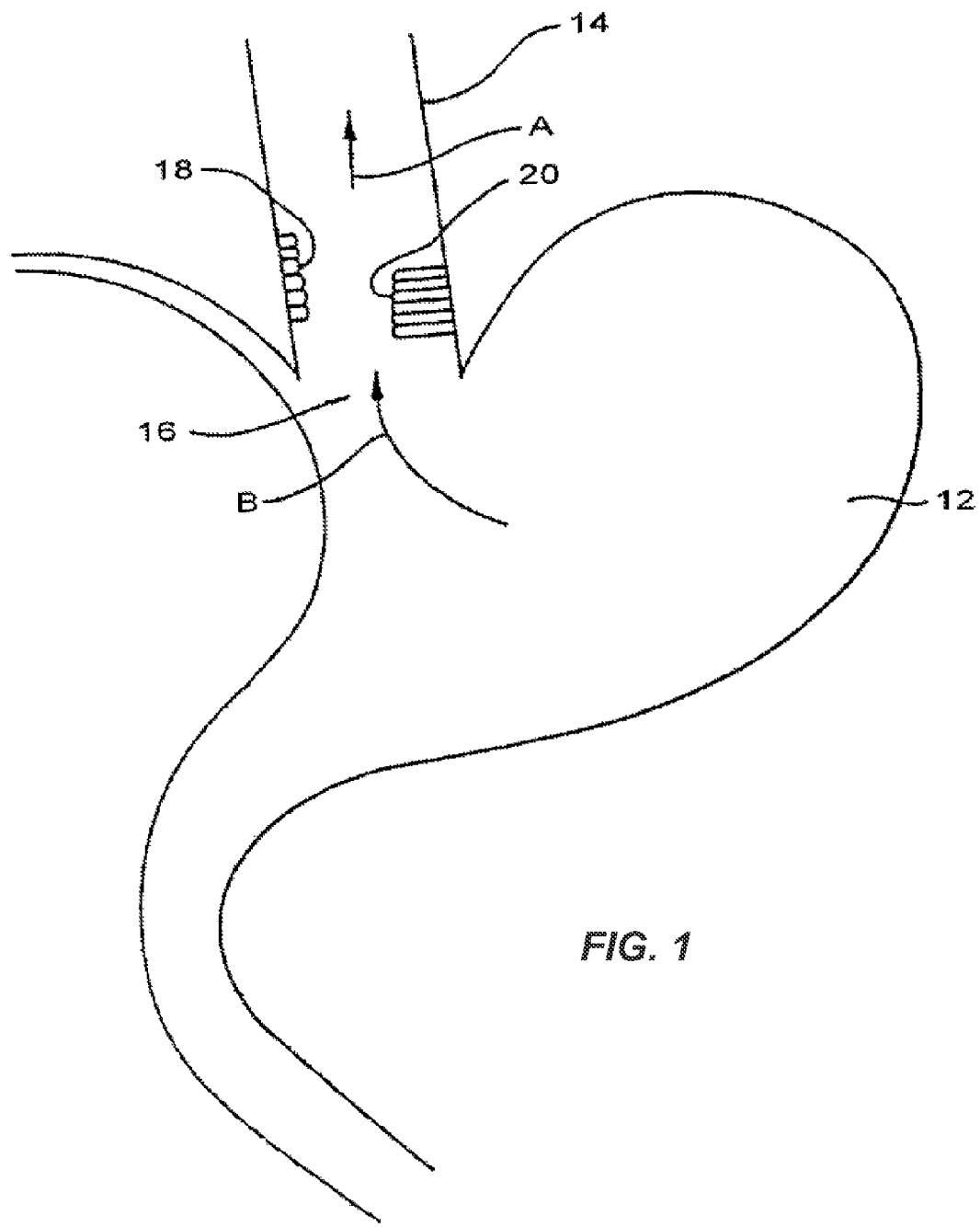
FIG. 1 is a schematic view of portions of an upper digestive tract in a human.

Certain disorders can cause the retrograde flow of gastric or intestinal contents from the stomach 12, into the esophagus 14, as shown by arrows A and B in FIG. 1. Although the causation of these problems are varied, this retrograde flow may result in secondary disorders, such as Barrett's Esophagus, which require treatment independent of and quite different from treatments appropriate for the primary disorder—such as disorders of the lower esophageal sphincter 16. Barrett's esophagus is an inflammatory disorder in which the stomach acids, bile acids and enzymes regurgitated from the stomach and duodenum enter into the lower esophagus causing damage to the esophageal mucosa. When this type of retrograde flow occurs frequently enough, damage may occur to esophageal epithelial cells 18. In some cases the damage may lead to the alteration of the squamous cells, causing them to change into taller specialized columnar epithelial cells 20. This metaplastic change of the mucosal epithelium from squamous cells to columnar cells is called Barrett's esophagus. Although some of the columnar cells may be benign, others may result in adenocarcinoma.

In one aspect, the present invention provides methods and systems for sizing the esophagus and treating the epithelium of selected sites of the esophagus in order to mitigate more severe implications for the patient. In many therapeutic procedures according to the present invention, the desired treatment effect is ablation of the tissue. The term "ablation" as used herein means thermal damage to the tissue causing tissue or cell necrosis. However, some therapeutic procedures may have a desired treatment effect that falls short of ablation, e.g. some level of agitation or damage that is imparted to the tissue to inure a desired change in the cellular makeup of the tissue, rather than necrosis of the tissue. With the present invention, a variety of different energy delivery devices can be utilized to create a treatment effect in a superficial layer of tissue, while preserving intact the function of deeper layers, as described hereafter.

Cell or tissue necrosis can be achieved with the use of energy, such as radiofrequency energy, at appropriate levels to accomplish ablation of mucosal or submucosal level tissue, while substantially preserving muscularis tissue. In a particular aspect, such ablation is designed to remove the entire mucosal lining in the treatment region, including the abnormal columnar growths 20 from the portions of the esophagus 14 so affected, and allow re-growth of a normal mucosal lining.

Figure 2:
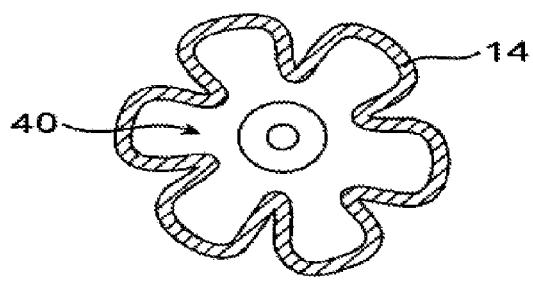
FIG. 2 is a cross sectional view of a device of the invention inserted in to an esophagus in its relaxed, collapsed state.

As illustrated in a cross-sectional view in FIG. 2, the esophagus in its collapsed, relaxed state does not form a perfect, cylindrical tube. Rather, the walls of the esophagus 14 undulate into a plurality of folds. In this state, the diameter of the esophagus is difficult to determine, especially by use of visualization techniques such as ultrasound or optical imaging. Additionally, uniform treatment of target tissue areas is also difficult because of the irregular surface contours of the esophageal wall.

Figure 3:
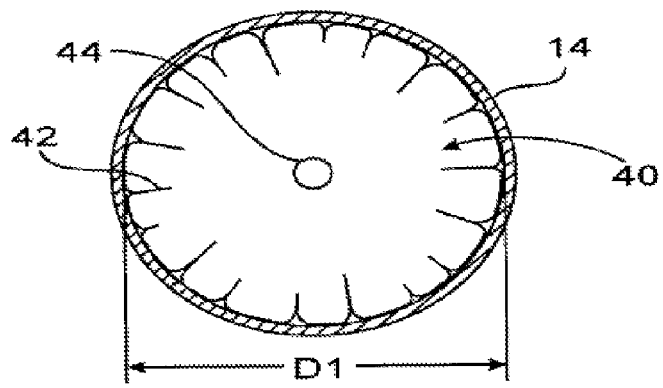
FIG. 3 is a cross-sectional view of a device of the invention deployed in an expanded configuration in the esophagus.
Figure 4:
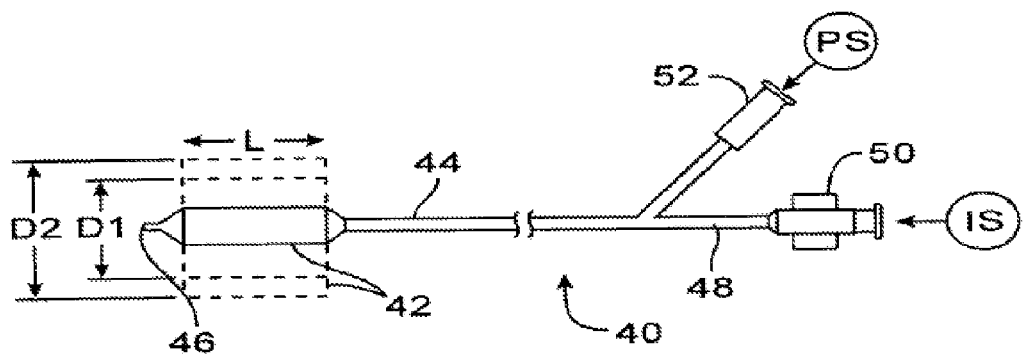
FIG. 4 is a schematic view of a sizing device of the invention.
Figure 5:
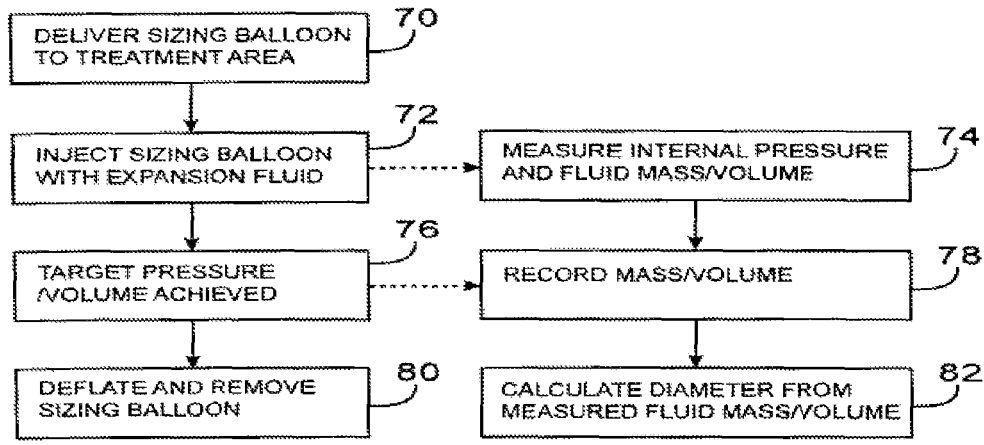
FIG. 5 is a flow chart of a method of the invention for sizing a luminal dimension.

In one embodiment of the invention, as illustrated in FIGS. 2, 3 and 4 and the flow chart of FIG. 5, a method is disclosed for utilizing a sizing device to measure luminal dimensions. The sizing device 40 is first delivered to the treatment region in the body lumen, as shown at block 70. For esophageal sizing as shown in FIG. 2, the esophagus 14 will be in a relaxed or collapsed configuration during delivery of the sizing device. The sizing device 40 is in a collapsed configuration during the delivery of the device to the treatment site in the esophagus. The low profile of the collapsed sizing device 40, as shown in FIG. 2, eases the delivery of the device into the esophagus and minimizes discomfort to the patient. Once the sizing device is oriented in the proper treatment area, an expansion fluid is injected into the balloon, as shown at block 72. The balloon is inflated until it engages the inside wall of the lumen, as shown in FIG. 3. During the infusion of the expansion medium, the extent of engagement of the balloon is monitored, as well as the amount of expansion medium being injected into the balloon, as shown by block 74. Once the balloon properly engages the lumen wall (shown at block 76), the final mass or volume of expansion medium is recorded so that the internal dimension of the esophagus may be calculated, shown at blocks 78, 82. The sizing balloon is then deflated so that it can be readily removed from the treatment site, shown at block 80.

Referring to FIGS. 2, 3, 4, a device of the present invention comprises a sizing device 40 for determining the dimensions of a treatment lumen. The device 40 has an expansion member 42 that is inserted into a lumen in a collapsed configuration and expanded upon proper placement at a pre-selected treatment area. In a preferred configuration, the expansion member 42 is a cylindrical balloon with a native diameter that is oversized so that it will be larger in its fully expanded configuration than the expected diameter of the treatment lumen. The balloon 42 comprises a thin, flexible, bladder made of a polymer material, for example polyimide, polyurethane, PET, or the like. The balloon is attached to a catheter sleeve 44, wherein the balloon is disposed on the distal end 46 of the catheter sleeve for infusing an expansion medium into the balloon from an infusion source IS. Infusion source is connected to an access port 50 of a y-connector located at the proximal end 48 of the catheter sleeve 44.

Ideally, the expansion medium comprises a compressible fluid, such as air. The expansion medium may alternatively comprise an incompressible fluid, such as water, saline solution, or the like. It would be understood by one of skill in the art that sizing a body lumen by monitoring the mass of an expansion medium advantageously can be accomplished using either compressible or incompressible fluids. Infusion of the expansion medium into the sizing balloon may be accomplished by a positive displacement device such as a fluid-infusion pump or calibrated syringe driven by stepper motor or by hand. Alternatively, for a compressible expansion medium, pressurized air or gas may also be used. In many embodiments, the sizing device also comprises a means for determining the amount of expansion fluid transferred to the balloon, such as a calibrated syringe. A mass or volume flow meter may be coupled to the fluid delivery source for simultaneously measuring the amount of fluid in the balloon as it is inflated.

As the expansion medium is injected into balloon 42, the balloon expands radially from its axis to engage the wall of the lumen. For esophageal treatment, the walls of the esophagus 14 unfold to form a more cylindrical shape as balloon 42 expands, as illustrated in FIG. 3. In this configuration, internal diameter D1 of the esophagus 14 is readily calculated based on the length L the balloon and the measured amount of expansion medium inside the balloon. Balloon 42 is oversized so that the diameter D2 of the balloon when unrestrained and fully inflated is larger than the diameter of the balloon when constrained in the lumen. Although an inflatable balloon is generally preferred, the sizing member may comprise a basket, plurality of struts, calipers, or the like instrument for determining the internal diameter of a tubular member.

Figures 7, 8:
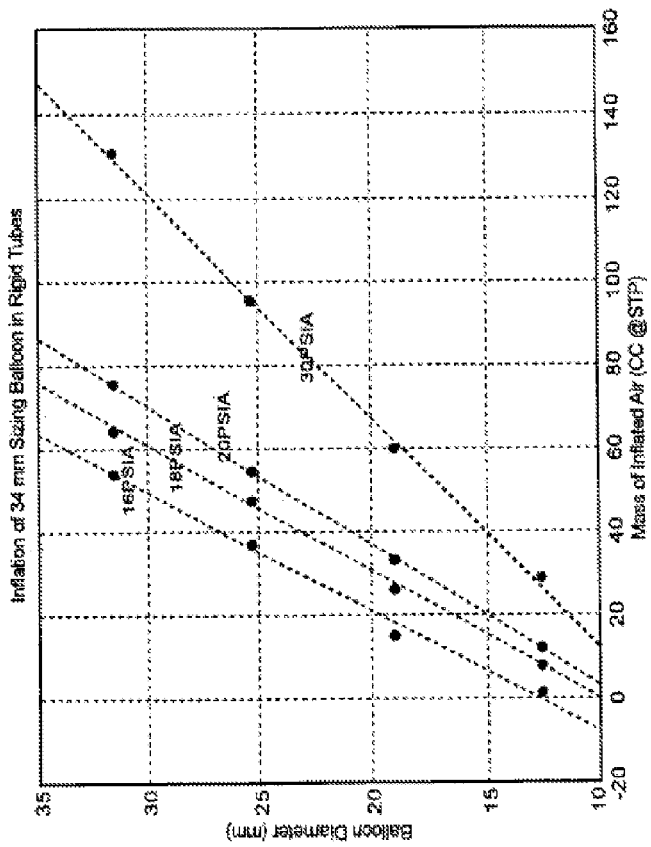
FIG. 7 is a chart of test results performed on calculating the diameter of a vessel by measuring the volume of air used to inflate the balloon.
FIG. 8 is a chart of test results for the air mass required to achieve various pressure levels in differently sized rigid containers.

Tests were performed to calculate the inside diameter of a member by using volume flow measurements. Various types and sizes of tubes were tested by measuring the mass of air used to inflate an oversized bladder inside the tube. As shown in FIG. 7, the diameter of the tube can be repeatably estimated by measuring the volume of air delivered into the balloon.

In some embodiments of the invention, a pressure sensor may be coupled to the sizing device, wherein the extent of engagement is determined by the internal pressure exerted from the expansion medium as measured by the pressure sensor or visual verification.

The pressure sensor may comprise any device for determining the pressure inside a vessel, such as a strain gauge. In FIG. 4, the pressure sensor PS is located at access port 52 at the proximal end of the catheter sleeve 44. Alternatively, the pressure sensor can be located inside the balloon 42. As the balloon expands to engage the wall of the lumen, the pressure in the balloon increases as a result of the constraint on the balloon from the lumen wall.

Because the balloon is oversized and not at its fully extended diameter when contacting the lumen wall, the pressure in the balloon is equal to the contact force per unit area against the lumen wall. Therefore, the pressure inside the balloon is directly proportional to the contact force on the lumen wall. Furthermore, the balloon may be expanded to apply pressure to the inside wall of the lumen, thereby causing the lumen to stretch. Generally, the sizing balloon will be inflated to a pressure corresponding to the desired pressure for treatment of the lumen. For esophageal treatment, it is desirable to expand the treatment device sufficiently to occlude the vasculature of the submucosa, including the arterial, capillary, or venular vessels. The pressure to be exerted to do so should therefore be greater than the pressure exerted by such vessels, typically from 1 psig to 10 psig, preferably from 4 psig to 7 psig and more preferably from 2 psig to 3 psig.

In some embodiments, the measurement of the pressure inside the balloon may be used to monitor the extent of engagement of the balloon with the lumen wall. Alternatively, the extent of engagement may be monitored by determining the expansion of the balloon via visual inspection with use of an endoscope, or by ultrasound, optical, or fluoroscopic imaging (not shown).

Tests were performed on different sized rigid tubes to calculate the amount of mass required to inflate an oversized balloon in a constrained tube at various pressures. As shown in FIG. 8, the test results showed predictable linear relationships between the measured inflated air mass and the tube diameter for each pressure range tested.

Figure 6:
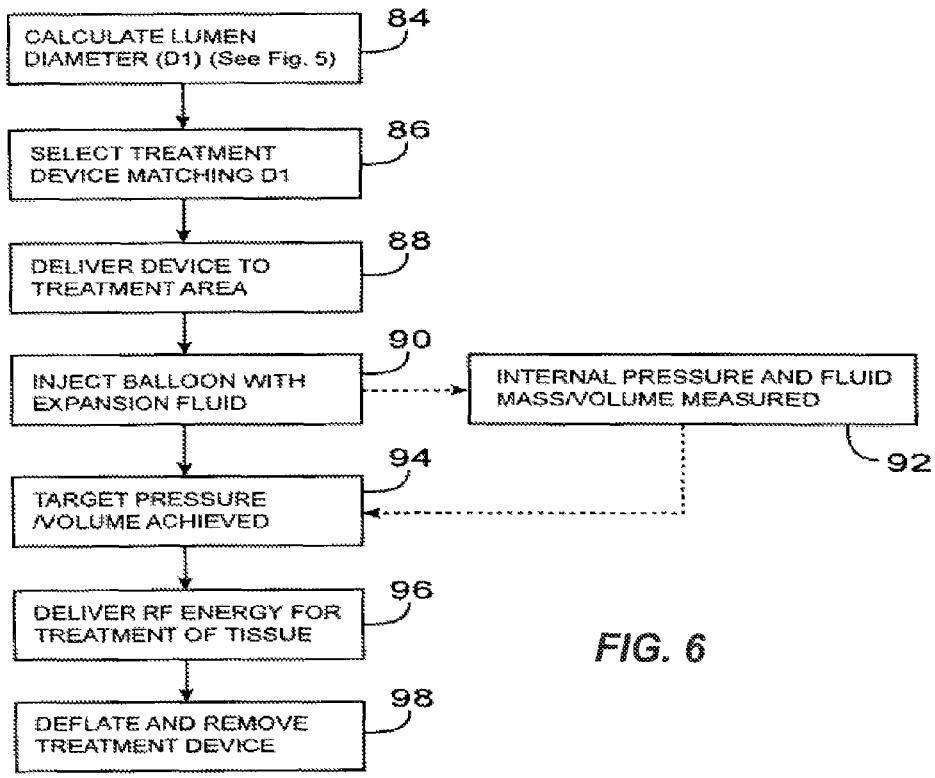
FIG. 6 is a flow chart of a method of the invention for treating luminal tissue

As shown in the flow chart of FIG. 6, a method and system of the present invention is disclosed for treating a luminal tissue. Similar to the method described in FIG. 5, a sizing device is used to calculate the internal diameter of the lumen, as shown at block 84. The measurement obtained from the sizing device is then used to select a treatment device from an array of different sized catheters, shown at block 86. The device is then inserted into the body lumen and delivered to the treatment site, as shown at block 88. An expansion fluid is then injected into the device by an infusion source like that of the sizing device as shown in block 90. Because the catheter is selected to have an outer diameter when fully expanded that appropriately distends the luminal wall, it is not necessary to monitor the expansion of the catheter. However, the pressure and fluid volume of expansion medium delivered to the treatment device can be monitored as a precautionary measure, as shown in blocks 92 and 94. With the catheter properly engaged to the luminal wall at the treatment site, energy, such as RF energy, is delivered to the catheter for treatment of the luminal tissue, as shown at block 96. Once treatment has been administered, the catheter is deflated for removal from the lumen as shown in block 98.

Figure 9:
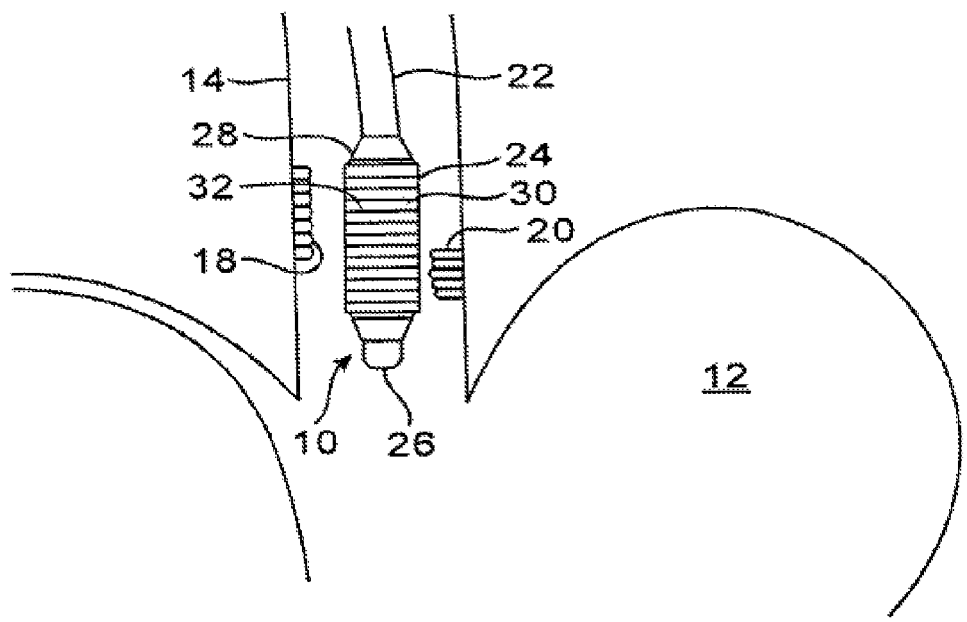
FIG. 9 is a schematic view of a treatment device of the invention in a compressed configuration in the esophagus.
Figure 10:
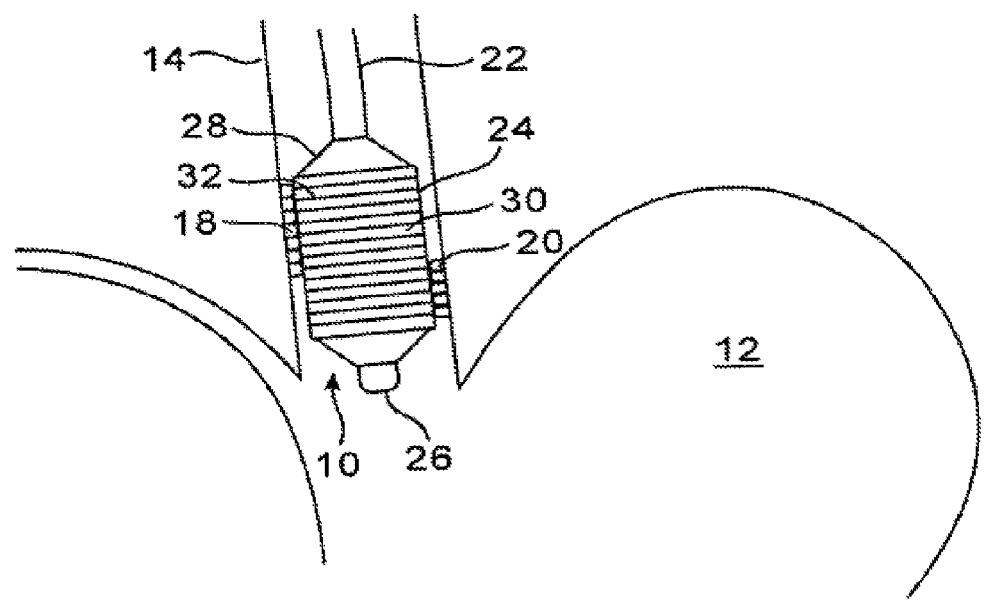
FIG. 10 is a schematic view of a treatment device of the invention in an expanded configuration in the esophagus.

As illustrated in FIGS. 9 and 10, a treatment device 10 constructed in accordance with the principles of the present invention, includes an elongated catheter sleeve 22 that is configured to be inserted into the body in any of various ways selected by the medical provider. For treatment of the esophagus, the treatment device may be placed, (i) endoscopically, e.g. through esophagus 14, (ii) surgically or (iii) by other means.

When an endoscope (not shown) is used, catheter sleeve 22 can be inserted in the en of the endoscope, or catheter sleeve 22 can be positioned on the outside of the endoscope. Alternately, an endoscope may be used to visualize the pathway that catheter 22 should follow during placement. As well, catheter sleeve 22 can be inserted into esophagus 1014 after removal of the endoscope.

An electrode support 24 is provided and can be positioned at a distal end 26 of catheter sleeve 22 to provide appropriate energy for ablation as desired. Electrode support 24 has a plurality of electrode area segments 32 attached to the surface of the support. The electrodes 32 can be configured in an array 30 of various patterns to facilitate a specific treatment by controlling the electrode size and spacing (electrode density). In various embodiments, electrode support 24 is coupled to an energy source configured for powering the array 30 at levels appropriate to provide the selectable ablation of tissue to a predetermined depth of tissue. The energy may be delivered circumferentially about the axis of the treatment device in a single step, i.e., all at one time. Alternatively, the energy may be delivered to different circumferential and/or axial sections of the esophageal wall sequentially.

In many embodiments, the support 24 may comprise a flexible, non-distensible backing. For example, the support 24 may comprise of a thin, rectangular sheet of polymer materials such as polyimide, polyester or other flexible thermoplastic or thermosetting polymer film. The support 24 may also comprise polymer covered materials, or other nonconductive materials. Additionally, the backing may include an electrically insulating polymer, with an electro-conductive material, such as copper, deposited onto a surface so that an electrode pattern can be etched into the material to create an array of electrodes.

Electrode support 24 can be operated at a controlled distance from, or in direct contact with the wall of the tissue site. This can be achieved by coupling electrode support 24 to an expandable member 28, which has a cylindrical configuration with a known, fixed length, and a diameter sized to match at its expanded state the calculated diameter of the expanded (not collapsed) lumen. Suitable expandable members include but are not limited to a balloon, non-compliant balloon, balloon with a tapered geometry, cage, frame, basket, plurality of struts, expandable member with a furled and an unfurled state, one or more springs, foam, bladder, backing material that expands to an expanded configuration when unrestrained, and the like. For esophageal treatment, it is desirable to expand the expandable member to distend the lumen sufficiently to occlude the vasculature of the submucosa, including the arterial, capillary, or venular vessels. The pressure to be exerted to do so should therefore be greater than the pressure exerted by such vessels, typically from 1 psig to 10 psig, preferably from 4 psig to 7 psig and more preferably from 2 psig to 3 psig. Generally, the expandable member for the treatment device will be selected to match the diameter measured by the sizing device at the desired pressure. Under this configuration, expansion of the expandable member will result in a pressure that properly distends the luminal wall. In some embodiments, it may be desirable to employ a pressure sensor or mass flow meter (not shown) as a precautionary measure so that over-distension of the lumen does not occur.

As shown in FIGS. 9 and 10, the electrode support 24 is wrapped around the circumference of expandable member 28. In one system of the present invention, a plurality of expandable members can be provided wherein the diameter of the expandable member varies from 12 mm to 50 mm when expanded. Accordingly, the system may include a plurality of electrode supports, each sized differently corresponding to the different sized expandable members. Alternatively, the electrode support 24 may be oversized to be at least large enough to cover the circumference of the largest expandable member. In such a configuration, the electrode support overlaps itself as it is wrapped around the circumference of the expandable member, similar to the electrode support of device 100 illustrated in FIG. 11, discussed infra.

In another embodiment, expandable member 28 is utilized to deliver the ablation energy itself. An important feature of this embodiment includes the means by which the energy is transferred from distal end 26 to expandable member 28. By way of illustration, one type of energy distribution that can be utilized is disclosed in U.S. Pat. No. 5,713,942, incorporated herein by reference, in which an expandable balloon is connected to a power source, which provides radio frequency power having the desired characteristics to selectively heat the target tissue to a desired temperature. Expandable member 28 may be constructed from electrically insulating polymer, with electro-conductive material, such as copper, deposited onto a surface so that an electrode pattern can be ached into the material to create an array of electrodes.

Electrode support 24 can deliver a variety of different types of energy including hut not limited to, radio frequency, microwave, ultrasonic, resistive heating, chemical, a heatable fluid, optical including without limitation, ultraviolet, visible, infrared, collimated or non-collimated, coherent or incoherent, or other light energy, and the like. It wilt be appreciated that the energy, including but not limited to optical, can be used in combination with one or more sensitizing agents.

The depth of treatment obtained with treatment device 10 can be controlled by the selection of appropriate treatment parameters by the user as described in the examples set forth herein. One important parameter in controlling the depth of treatment is the electrode density of the array 30. As the spacing between electrodes decreases, the depth of treatment of the affected tissue also decreases. Very close spacing of the electrodes assures that the current and resulting ohmic heating in the tissue is limited to a very shallow depth so that injury and heating of the submucosal layer are minimized. For treatment of esophageal tissue using RF energy, it may be desirable to have a width of each RF electrode to be no more than, (i) 3 min, (ii) 2 mm, (iii) 1 mm (iv) 0.5 mm or (v) 0.3 mm (vi) 0.1 mm and the like. Accordingly, it may be desirable to have a spacing between adjacent RF electrodes to be no more than, (i) 3 mm, (ii) 2 mm, (iii) 1 mm (iv) 0.5 mm (v) 0.3 mm (vi) 0.1 mm and the like. The plurality of electrodes can be arranged in segments, with at least a portion of the segments being multiplexed. An RF electrode between adjacent segments can be shared by each of adjacent segments when multiplexed.

Figure 13A:
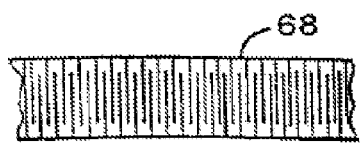
FIG. 13a-c shows the electrode pa that may be used with a treatment device of the invention.
Figure 13B:
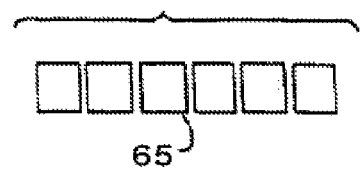
Figure 13C:
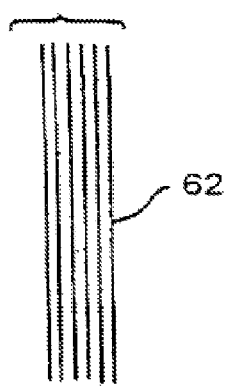
Figure 14A:
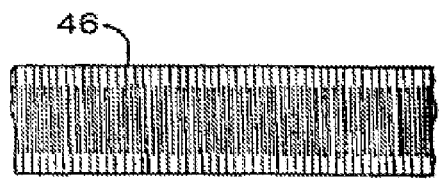
FIG. 14a-d shows additional electrode patterns that may be used with a treatment device of the invention.
Figure 14B:
Figure 14D:
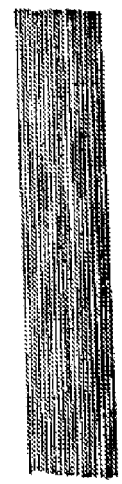
Figure 14C:
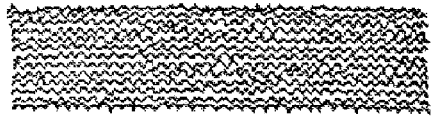

The electrode patterns of the present invention may be varied depending on the length of the site to be treated, the depth of the mucosa and submucosa, in the case of the esophagus, at the site of treatment and other factors. The electrode pattern 30 may be aligned in axial or traverse direction across the electrode support 24, or formed in a linear or non-linear parallel matrix or series of bipolar pairs or monopolar electrodes. One or more different patterns may be coupled to various locations of expandable member 28. For example, an electrode array, as illustrated in FIGS. 13(a) through 13(c), may comprise a pattern of bipolar axial interlaced finger electrodes 68, six bipolar rings 62 with 2 mm separation, or monopolar rectangles 65 with 1 mm separation. Other suitable RF electrode patterns which may be used include, without limitation, those patterns shown in FIGS. 14(a) through 14(d) as 54, 56, 58 and 60, respectively. Pattern 54 is a pattern of bipolar axial interlaced finger electrodes with 0.3 mm separation. Pattern 56 includes monopolar bands with 0.3 mm separation. Pattern 60 includes bipolar rings with 0.3 min separation. Pattern 58 is electrodes in a pattern of undulating electrodes with 0.2548 mm separation.

A probe sensor may also be used with the system of the present invention to monitor and determine the depth of ablation. In one embodiment, one or more sensors (not shown), including but not limited to thermal and the like, can be included and associated with each electrode segment 32 in order to monitor the temperature from each segment and then be used for control. The control can be by way of an open or closed loop feedback system. In another embodiment, the electroconductive member can be configured to permit transmission of microwave energy to the tissue site. Treatment apparatus 10 can also include steerable and directional control devices, a probe sensor for accurately sensing depth of ablation, and the like.

Figure 11:
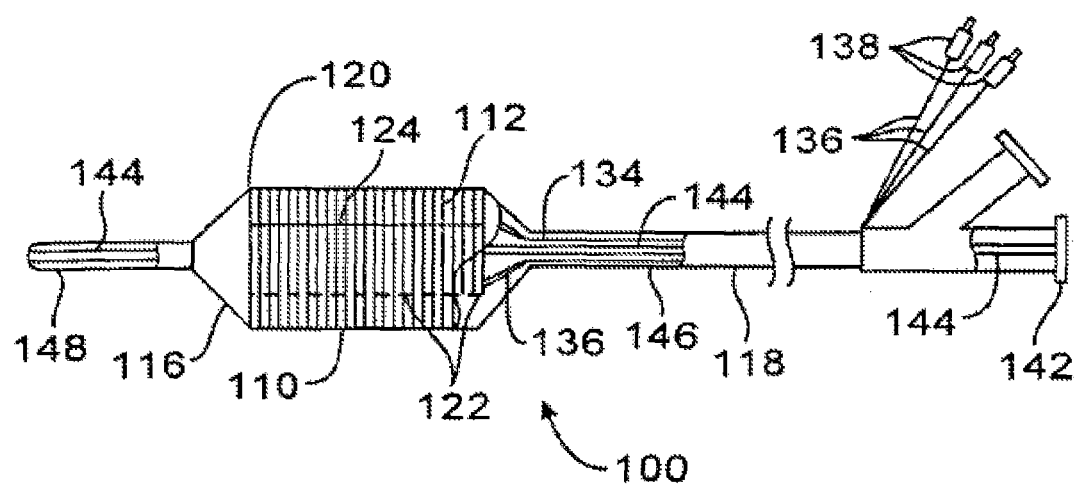
FIG. 11 is a schematic view of another embodiment of a treatment device of the invention.

Referring to FIG. 11, one embodiment of the invention comprises an electrode deployment device 100 having an electrode support 110 furled around the outside of an inflatable balloon 116 that is mounted on a catheter sleeve 118. Support 110 has an electrode array 112 etched on its surface, and is aligned between edges 120 that intersect the taper region located at the distal and proximal ends of balloon 116. Support 110 may be attached at a first end 122 to balloon 116 with an adhesive. The second end 124 of the support is furled around the balloon, overlapping the first end 122. Alternatively, support 110 may be retained in a compressed furled state around balloon 116 by an elastic band. In such a configuration, the adhesive need not be applied to attach first end 122 to balloon 116, thus allowing for rapid placement or exchange of the appropriately sized balloon 116 to match measurements made from the sizing device 10 illustrated in FIG. 4.

Figure 12:
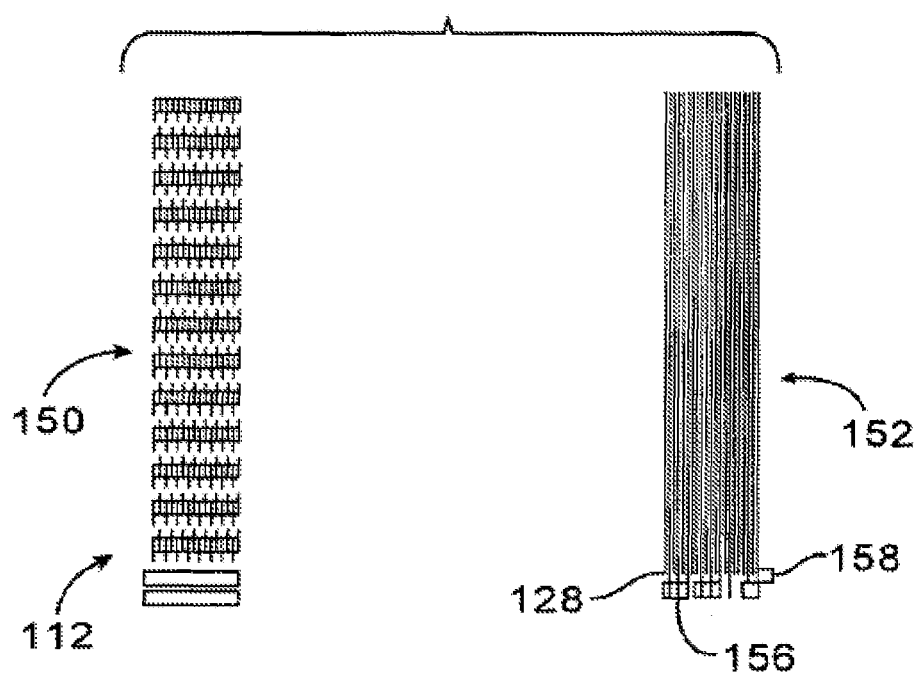
FIG. 12 shows a top view and a bottom view of an electrode pattern of the device of FIG. 11.

FIG. 12 shows a bottom view 150 and a top view 152 of the electrode array 112 of support 110. In this embodiment, the array 112 has 20 parallel bars, 0.25 mm wide, separated by gaps of 0.3 mm. The bars on the circuit form twenty complete continuous rings around the circumference of balloon 116. Electrode array 112 can be etched from a laminate consisting of copper on both sides of a polyimide substrate. One end of each copper bar has a small plated through hole 128, which allows signals to be passed to these bars from 1 of 2 copper junction blocks 156 and 158, respectively, on the back of the laminate. One junction block 156 is connected to all of the even numbered bars, while the other junction block 158 is connected to all of the odd numbered bars.

As shown in FIGS. 11 and 12, each junction block 156 and 158 is then wired to a bundle of AWG wires 134. The wiring is external to balloon 116, with the distal circuit wires affixed beneath the proximal circuit. Upon meeting the catheter sleeve of the device, these bundles 134 can be soldered to three litz wire bundles 136. One bundle 136 serves as a common conductor for both circuits while the other two bundles 136 are wired individually to each of the two circuits. The litz wires are encompassed with heat shrink tubing along the entire length of the catheter sleeve 118 of the device. Upon emerging from the proximal end of the catheter sleeve, each of these bundles 136 is individually insulated with heat shrink tubing before terminating to a mini connector plug 138. Under this configuration, power can be delivered to either or both of the two bundles so that treatment can be administered to a specific area along the array.

The y connector 142 at the proximal end of the catheter sleeve includes access ports for both the thru lumen 144 and the inflation lumen 146. The thru lumen spans the entire length of the balloon catheter and exits through lumen tip 148 at the distal end of balloon 116. The inflation lumen 146 is coupled to balloon 116 so that the balloon can be inflated by delivery of a liquid, gaseous solution such as air or the like.

In some embodiments, for delivery of apparatus 100, support 110 is tightly furled about deflated balloon 116 and placed with in a sheath (not shown). During deployment, this sheath is retracted along the shaft to expose support 110. In alternative embodiments, an elastic member (not shown) may be coupled to the support 110 to keep the support furled around balloon 116 during deployment of apparatus 100.

In order to ensure good contact between the esophageal wall and electrode array 112, slight suction may be applied to the through lumen tube to reduce the air pressure in the esophagus 14 distal to balloon 116. The application of this slight suction can be simultaneously applied to the portion of the esophagus 14 proximal to balloon 116. This suction causes the portion of the esophageal wall distended by balloon 116 to be pulled against electrode arrays 112 located on balloon 116.

Apparatus 100, illustrated in FIG. 11, is designed for use with the RF energy methods as set forth herein. Electrode array 112 can be activated with approximately 300 watts of radio frequency power for the length of time necessary to deliver an energy density from 1 $J/cm^2$ to 50 $J/cm^2$. To determine the appropriate level of energy, the diameter of the lumen is evaluated so that the total treatment area can be calculated. A typical treatment area of 10 $cm^2$ will require total energy ranging from 10 J to 500 J. In one embodiment, controlling the depth of treated tissue can include normalizing the amount of power delivered to the tissue over time. In this context, normalizing power delivered means equivalent power densities (i.e., power unit area of electrode surface area $\{W/cm^2\}$) are delivered to esophagi of differing diameters. In another embodiment, controlling the depth of treated tissue comprises controlling the amount of delivered energy density. Such can be accomplished by normalizing the amount of energy delivered to tissue over time so that equivalent energy densities (i.e., energy per unit area of electrode surface area $\{J/cm^2\}$) are delivered to esophagi of differing diameters.

In order to effectively ablate the mucosal lining of the esophagus and allow re-growth of a normal mucosal lining without creating damage to underlying tissue structures, it is preferable to deliver the radiofrequency energy over a short time span in order to reduce the effects of thermal conduction of energy to deeper tissue layers, thereby creating a "searing" effect. It is preferable to deliver the radiofrequency energy within a time span of less than 5 seconds. An optimal time for effective treatment is less than 1 second and preferably less than 0.5 second or 0.25 second. The lower bound on time may be limited by the ability of the RF power source to deliver high powers, or alternatively by the required depth of treatment. Since the electrode area and consequently the tissue treatment area can be as much as several square centimeters, RF powers of several hundred watts would be required in order to deliver the desired energy density in short periods of time. This may pose a practical limitation on the lower limit of time. However, an RF power source configured to deliver a very short, high power, pulse of energy could be utilized. Using techniques similar to those used for flash lamp sources, or other types of capacitor discharge sources, a very high power, short pulse of RF energy can be created. This would allow treatment times of a few msec, or less. While this type of approach is feasible, in practice a more conventional RF source with a power capability of several hundred watts may be preferred.

The energy source may be manually controlled by the user and is adapted to allow the user to select the appropriate treatment time and power setting to obtain a controlled depth of ablation. The energy source can be coupled to a controller (not shown), which may be a digital or analog controller for use with the energy source, including but not limited to an RF source, or a computer with software. When the computer controller is used it can include a CPU coupled through a system bus. The system may include a keyboard, a disk drive, or other non volatile memory system, a display and other peripherals known in the art. A program memory and a data memory will also be coupled to the bus.

in some embodiments of the present invention, systems and methods are disclosed for treating luminal tissue with a single treatment device that variably expands to accommodate a number of different sized lumens. Preferably, the treatment device comprises a furled electrode support that variably engages the luminal wall while keeping the electrode density constant. Such approaches are described in detail in co-pending application Ser. No. 10/754,444, the full disclosure of which is incorporated herein by reference. For example, for the treatment device 100 shown in FIG. 11, which employs a variable exposed-length electrode array 112, balloon 116 may be oversized with respect to the size of the lumen so that it can be expanded to accommodate differing luminal dimensions from patient to patient. Measurements from sizing device 10 can be used to scale as needed the desired power and energy settings to deliver the same power and energy per unit area. These changes can be made either automatically or from user input to the RF power source. If different treatment depths are desired, the geometry of electrode array 112 can be modified to create either a deeper or more superficial treatment region. Making the electrodes of array 112 more narrow and spacing the electrodes closer together reduces the treatment depth. Making the electrodes of array 112 wider, and spacing the electrodes further apart, increases the depth of the treatment region. Non-uniform widths and spacings may be exploited to achieve various treatment effects.

Figure 15:
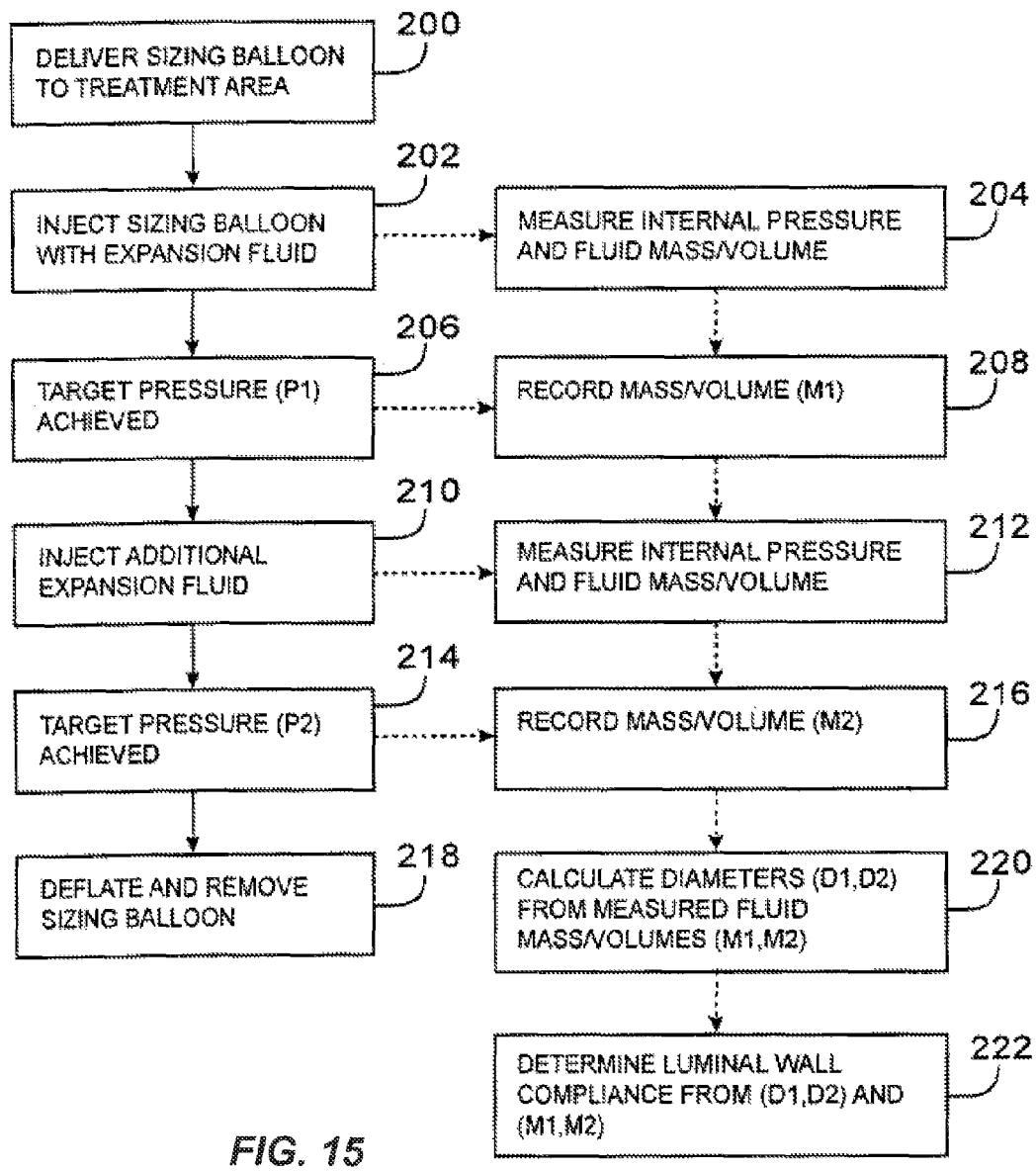
FIG. 15 shows a flow chart of a method of the invention for determining the wall compliance of a lumen.

Referring to FIG. 15, the sizing device may be used as a method for determining the lumen diameter and wall compliance of one or more sections of the esophagus. A sizing device having an inflatable balloon like that of device 40 illustrated in FIG. 5 is inserted into the esophagus in a compressed configuration and positioned at a location within the esophagus, as shown at block 200. The balloon is then inflated with a compressible fluid so that the balloon engages the inside wall of the esophagus and distends the wall of the esophagus, shown at block 202. While the expansion medium is delivered to the balloon, the static pressure inside the balloon is monitored with a pressure sensor and the amount of expansion medium delivered to the balloon is measured, shown at block 204. The pressure may be measured at the infusion source with strain gauge or the like. Alternatively, the pressure can be measured at a location inside the balloon with a microminiature pressure transducer or the like. The amount of expansion medium delivered to the balloon may be measured by a mass-flow meter or the like. Once a first target pressure (P1) inside the balloon is achieved, a corresponding first mass or volume measurement (M1) is recorded, as shown at blocks 206 and 208. The values of P1 and M1 are used to calculate the lumen diameter at pressure P1, using the relationship previously determined and shown in FIG. 8, block 200 of FIG. 15, or other equivalent means. Additional expansion medium is then delivered to the balloon, and the static pressure and the total amount of expansion medium within the balloon are monitored, shown at blocks 210 and 212. This continues until a second target pressure (P2) inside the balloon is achieved, and a corresponding second mass or volume measurement (M2) is recorded, as shown at blocks 214 and 216. Calculation of the lumen diameter at pressure P2 is performed as previously described and shown in block 220. The sizing balloon is then deflated and then removed from the esophagus as shown in block 218. Target pressure values P1 and P2 are generally set at values that cause the esophagus to distend, but not overdistend. Typical target pressure values range from 1 psig to 7 psig, preferably from 4 psig to 7 psig and more preferably from 2 psig to 3 psig. Wall compliance of the esophagus is then determined based on the variation in the calculated lumen diameter between a first measured pressure P1 and a second measured pressure P2, as shown in block 222.

Figure 21:
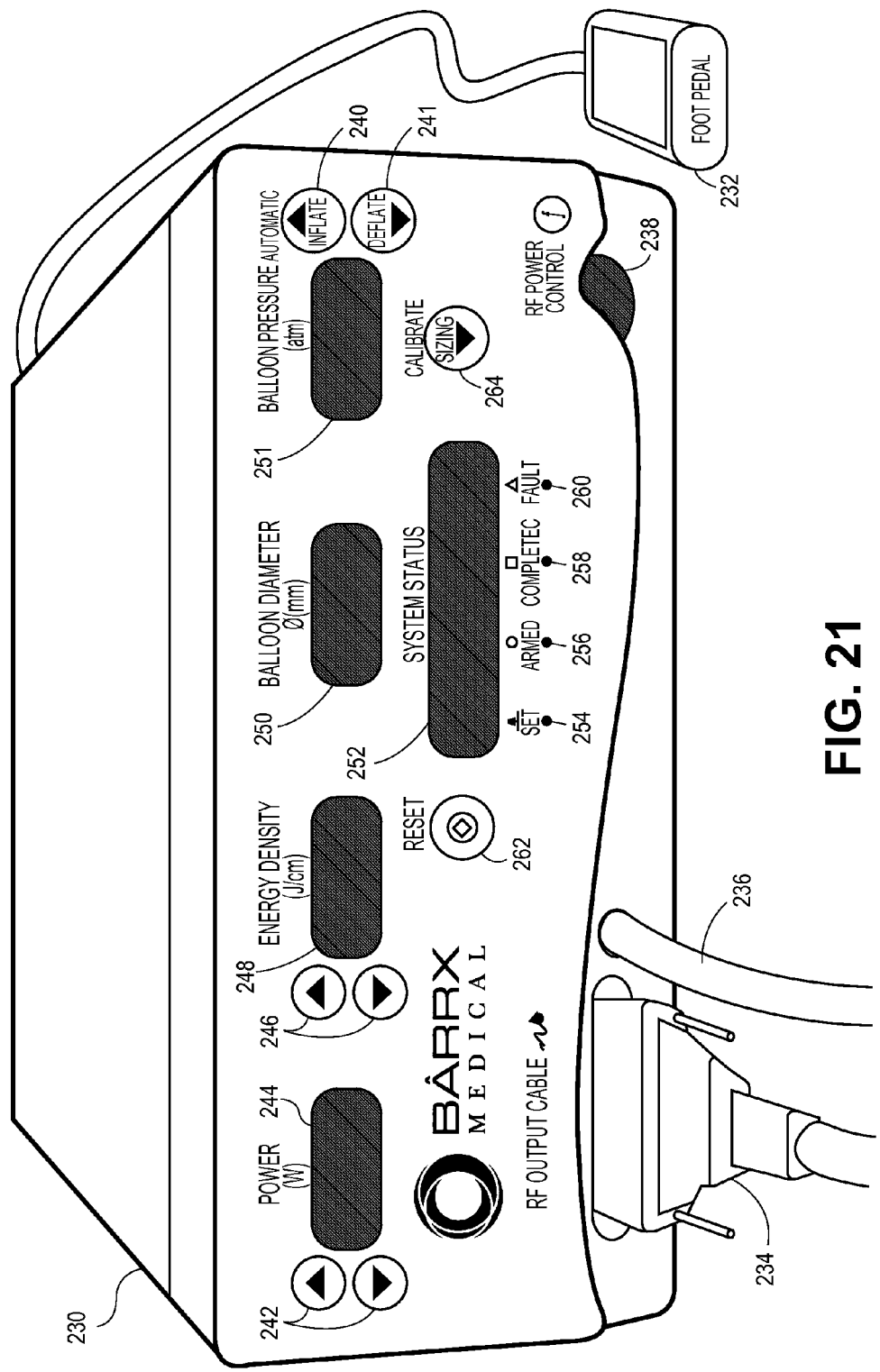
FIG. 21 illustrates an exemplary front panel of the generator.

FIG. 21 is an exemplary front panel of a generator system according to one embodiment of the invention. In one embodiment, the generator 230 produces, delivers and controls power, such as RF power. Other functions of the generator 230 include controlling inflation and deflation of the sizing balloon, estimating the diameter of the sizing balloon, selective delivery of RF power and energy to a treatment catheter and specific electrodes within the treatment catheter, and displaying various information to a user. To deliver various information regarding use parameters and status of the system, the front panel of the generator 230 incorporates various controls, displays and indicators.

The generator 230 connects to the catheter 22 through the RF and communication (Python) cable 234. When the generator 230 is connected to a catheter, the generator is capable of detecting whether it is a sizing catheter, used for determining the size of the esophagus, or a treatment catheter, used for ablation. The generator 230 reads from a storage device the type of catheter that is connected thereto. The storage device stores various catheter specific information and sizing specific parameters. For example, the storage device contains various generator settings for each diameter ranges. Further, the generator 230 may cause additional information to be stored, recommended catheter size after balloon auto-sizing is performed or the number of ablations performed. It should be noted that the storage device may be any suitable storage device, such as an EEPROM.

When the generator 230 detects a sizing catheter, the generator 230 performs an estimation of the balloon diameter. In order to reduce uncertainty in the diameter measurement, a calibration of the balloon may be performed, using control 264. During calibration, the volume of gas needed to fully expand the unconstrained balloon is determined, and will be used to determine a calibration constant. Using a mass flow sensor, the generator 230 measures the total gas or fluid mass required to inflate the sizing balloon to a specific pre-determined pressure. This predetermined pressure is a clinically safe pressure to perform the sizing of the esophagus and is chosen to ensure that inflation of the balloon within the esophagus would not rupture the esophagus while stretching and smoothing its lining. In order to initially evacuate all the gas in the balloon, the balloon is inflated to a pressure of approximately 4 psig, then deflated to a negative pressure of approximately up to −4 psig, and then inflated again to about 4 psig. Fluid or gas is delivered to the balloon using a pneumatic connection cable 236. Upon depression of the automatic inflation button 240, the generator will deliver air to the balloon according the sizing catheter inflation pressure. It should be noted that the balloons on either the treatment catheter or the sizing catheter may be inflated or deflated using the control buttons 240 and 241. While the balloon is inflated, the balloon pressure may be continuously displayed on display 251.

Before inserting the sizing balloon in the esophagus to measure its effective diameter at a given inflation pressure (nominal 4 psig) each balloon is first calibrated in air. The calibration process involves attaching the sizing balloon to the pneumatic connection cable 236 and generator 230 and first pulling a vacuum (typical pressure values range from 0 to −6 psig, nominal −4 psig) to fully collapse the balloon. Next a mass flow sensor of the generator 230 is used to accurately measure the amount of air necessary to fill the balloon (nominal 33.7 mm diameter) to 4 psig, thereby solving the relationship between volume and pressure for that balloon size and shape. This calibration information subsequently enables diameter measurements of the esophagus by measuring the amount of air necessary to inflate the balloon to a specific diameter.

Once balloon calibration is complete, the sizing balloon is introduced in the esophagus and repositioned at various locations within the esophagus. For each one of these locations, the generator 230 estimates the diameter of the balloon and effectively the esophagus diameter at the set pressure and then automatically recommends an ablation balloon catheter diameter to be subsequently used. The generator 230 will then display the recommended balloon diameter on display 250. After auto-sizing is performed, the system will automatically deflate the sizing catheter balloon to a negative pressure of approximately −2 psig or less.

Figure 16:
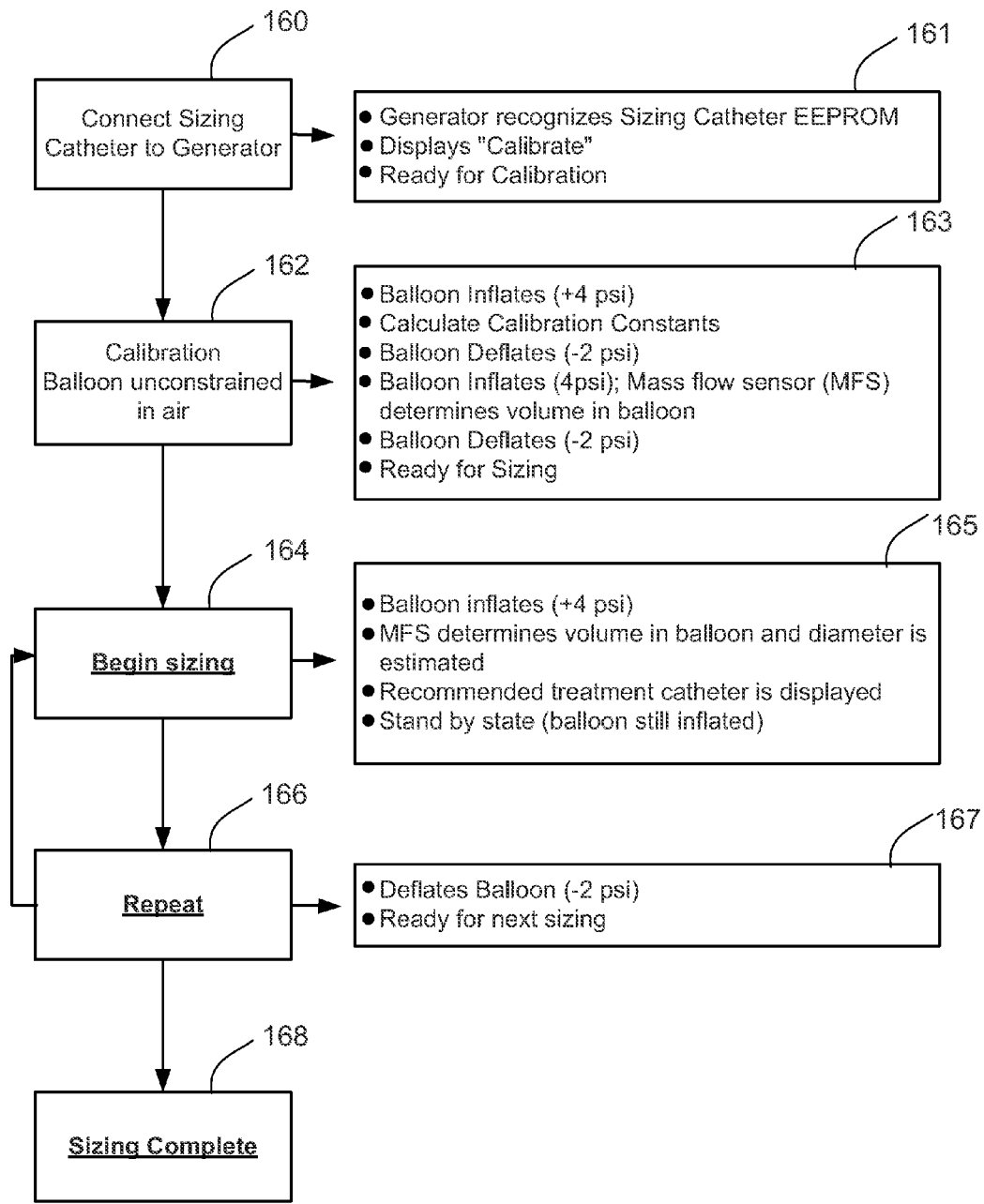
FIG. 16 illustrates a flow chart of a method for size estimation.

FIG. 16 is an exemplary flow chart of the method for measuring the size of the esophagus and finding the most proximal Barrett's esophagus location or other areas to be ablated. At step 160, a sizing catheter is connected to the generator. The specific characteristics of the sizing catheter are recognized by the generator from the storage device, such as: whether and when the catheter has been used before, and whether the balloon has already met a maximum number of allowed inflations. The system is ready for calibrating the balloon at step 161 if the catheter and the balloon are optimal for use. For better accuracy, the balloon is unconstrained in air during calibration. At step 163, the balloon goes through the inflate-deflate-inflate cycle such that the mass flow sensor determines the volume in the balloon at a pre-set pressure. When calibration is complete, the balloon automatically deflates and is introduced into the esophagus for sizing, as shown at step 164. The balloon is inflated again inside the esophagus at various locations to estimate the inner diameter of the esophagus. At step 165, a first size is displayed and a stand by state is indicated on the front panel of the generator. The sizing routine is repeated at various locations in the esophagus to find the location of the abnormal cells and determine the recommended catheter size, as shown in steps 166, 167 and 168. The generator 230 stores various information obtained throughout the sizing process, such as the estimated diameter of the esophagus, the calibration balloon volume, the number of sizing performed and the measured diameters.

Figure 17:
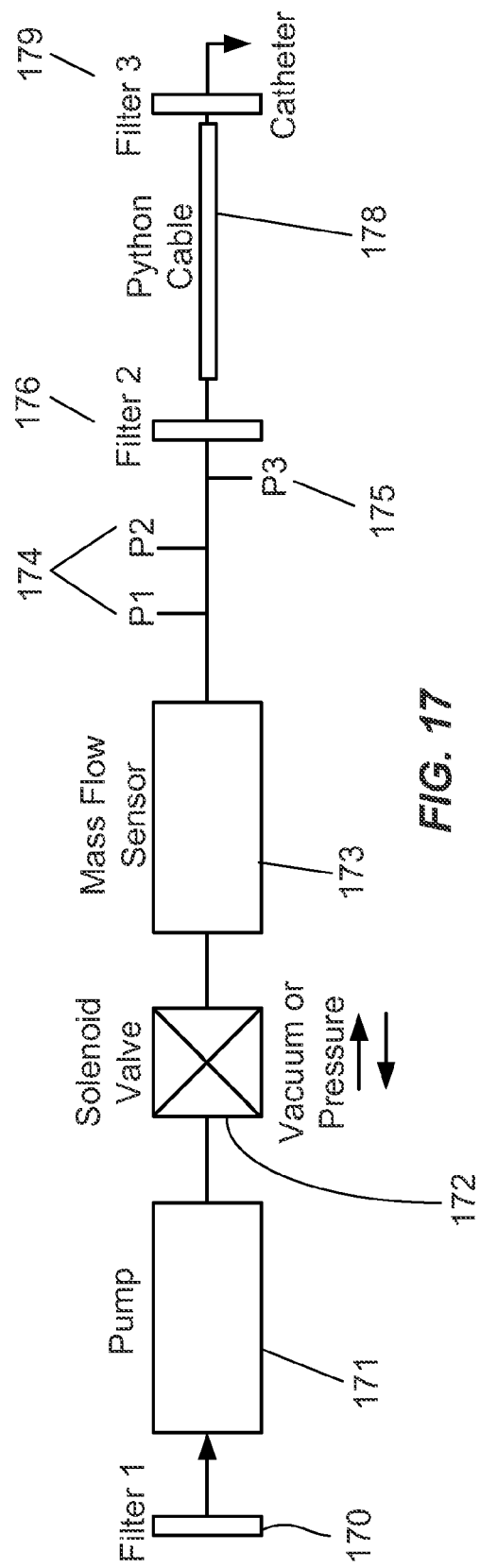
FIG. 17 illustrates an exemplary schematic of a mechanism for performing balloon sizing using a mass flow meter and pressure sensors.

FIG. 17 illustrates a schematic of an exemplary mechanism for performing balloon sizing using a mass flow meter and pressure sensors. Using this mechanism, the generator 230 monitors and controls the pressure in the balloon and estimates the volume within the balloon. Pump 171 supplies compressed air to the solenoid valve 172, which can switch the flow of air for either inflating or deflating the balloon. Prior to the gas entering the pump 171, filter 170 removes particulates from the gas that will enter the pump 171. The mass flow sensor 173 senses the mass of air coming in the system. In addition, the flow sensor 173 could be used to measure the flow of air out of the system for enhanced safety and accuracy of the system. The pressure within the system is measured by pressure sensors 174 and 175, with sensor 175 measuring the atmospheric pressure. Alternatively, instead of sensing the pressure within the system, a positive displacement pump may be used to pump a known amount of fluid or gas into the balloon. When the balloon is deflated, the air flows from the inside of the balloon to the mass flow sensor 173. Filters 176 and 179, connected by Python cable 178, prevent contamination of the mass flow sensor 173 and pump 171 during deflation.

It should be noted that the sizing method and system described herein may be used for estimating the inner diameter or other cross-sectional parameters of any body lumens or passageways, for example for lumens within the gastrointestinal tract, vasculature, urinary tract, urogenital system or pulmonary system.

Once the size of the esophagus is estimated for a set pressure, an appropriate treatment catheter is connected to the generator in order to ablate abnormal cells within the esophagus. The diameter of the balloon of the attached treatment catheter is read from the storage device. It should be noted that, in an alternate embodiment, treatment of the esophagus may be performed using the same catheter and balloon used for sizing. In such embodiment, the generator would recognize the catheter's dual function, sizing/treatment, and would read the appropriate parameters from the storage device.

Referring to FIG. 21, after the ablation balloon diameter is read from the storage device, the diameter is displayed on display 250. Based on the recommended size of the treatment catheter, the appropriate generator settings are retrieved from the storage device, such as: balloon inflation pressure, balloon volume data, default, maximum or minimum power settings, default, maximum or minimum energy settings, or size of the electrodes. Thus, the energy density and power levels can be automatically set according to the size of the treatment catheter. The preset power level is displayed on display 244, while the preset energy density level is displayed on display 248.

The generator 230 then inflates the balloon of the attached treatment catheter to a preset pressure of approximately 7 psig, which will be displayed on display 251. The set indicator 254 indicates the unit is in stand-by mode, when all the values are being set. In the standby mode, all the set values are displayed. Throughout the entire ablation procedure, it is desirable to maintain the pressure on the balloon at a steady pressure as a safety precaution. If the balloon stays at a pressure of at least 6.5 psig (typical pressure values range from 0.5-200 psig), the system is then considered "armed." The arm indicator 256 indicates that the displayed values are the set values and the system is ready to deliver RF energy. The RF on/off switch 238 indicates and controls when RF power is being delivered. In one embodiment, the generator 230 delivers and controls power until the desired energy density is delivered. The generator maintains a set power on each electrode and is capable of sequentially delivering energy to each electrode on the treatment catheter. When the desired energy is delivered to all the desired locations, the completed indicator 258 indicates the ablation is completed.

A user may have the capability to adjust the power and the energy density delivered to the tissue. The output power can be set and adjusted using the up and down buttons 241. The actual power delivered to the tissue from the catheter leads is displayed on the power display 244. Similarly, the energy density is set using the up and down button 246 and the output energy density delivered is displayed on the LED display 248.

The system status display 252 is an LCD panel and displays operational codes and user instructions. For example, the panel 252 displays the "Calibration" function prior to performing auto-sizing of the balloon. The panel 252 also displays error codes and an error message with instructions for solving errors. The reset button 262 may be pressed to reset the system if an error occurs. Further, the panel 252 indicates when the system is in standby mode. The fault indicator 260 indicates when the system is in the fault mode and a non-recoverable error was detected. It should be noted that the front panel of the generator 230 may display, control and indicate functions other than the exemplary functions described herein.

In one embodiment, pedal-type footswitch 232 is attached to the generator rear panel and may control the inflation system and RF delivery. The pedal 232 is capable of duplicating certain functions of the generator front panel buttons. For example the footswitch 232 may duplicate the RF on/off button 238 and/or the balloon auto inflation up and down buttons 240 and 241.

Figure 18:
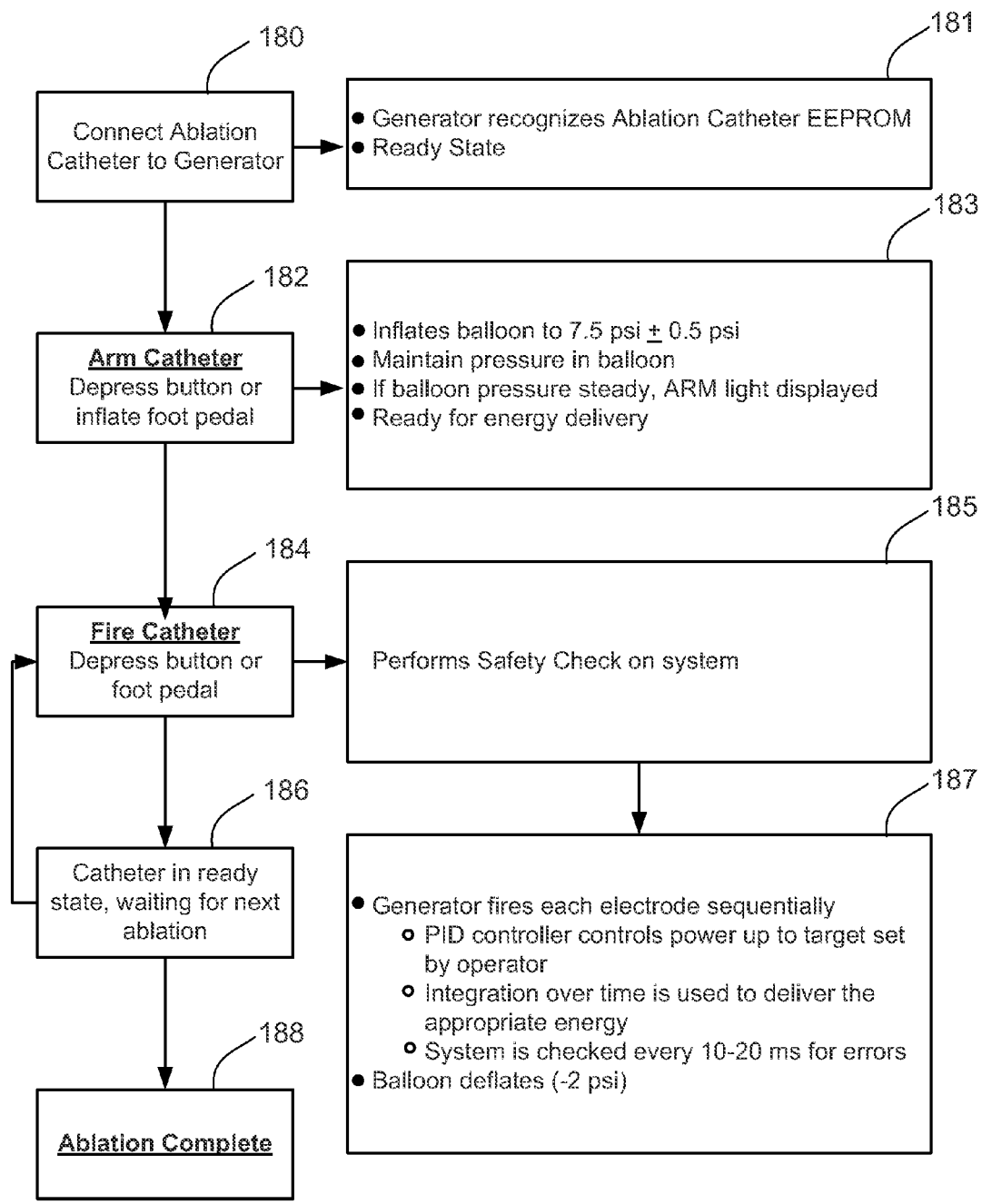
FIG. 18 is an exemplary flowchart of the ablation method.

FIG. 18 is an exemplary flowchart of the ablation procedure according to one embodiment of the invention. When the ablation catheter is connected to the generator, at step 180, the generator recognizes the specific characteristics of the ablation catheter and is ready to inflate the balloon, at step 181. The catheter is armed at 182 and the balloon is inflated and maintained at a pressure of approximately 7 psig (typical pressure values range from 0.5 to 200 psig). If the balloon pressure is steady, the ARM indicator is fit on the front panel display of the generator. At step 183, once the ARM tight is on, the generator is ready for delivering energy to the electrodes of the ablation catheter. The energy is subsequently automatically delivered by the generator 230, as shown at step 184. After each ablation, the balloon is automatically deflated in order to reposition the balloon and the electrodes to another ablation location within the esophagus. A series of subsequent ablations are performed as needed at step 186. After treating all the desired locations within the esophagus, the ablation is complete at step 188.

It should be noted that the generator delivers energy only after the system meets certain safety checks, as shown at steps 185 and 187. The generator periodically monitors balloon inflation, energy parameters and overall system integrity before and during the tissue treatment. These safety procedures ensure that the generator can safely deliver the required power. For example, the generator will not deliver power to the electrodes unless the impedance and temperature of the tissue are within acceptable parameters. Similarly, the generator monitors any pressure fluctuations within the treatment balloon. In one embodiment, the generator 230 will only deliver power if the balloon inside the esophagus is maintained at a steady required pressure of approximately 7+/−1 psig. This safety check ensures that there is no connection leak or balloon leak and the esophagus is fully distended prior to ablation. Another precaution is taken with respect to deflation of the balloon between ablations. In order to ensure that the balloon is fully deflated before repositioning it to a different location within the esophagus, the balloon is deflated to a pressure of approximately −2 psig.

in one embodiment, the generator 230 monitors and controls the power output to the electrodes and ensures that a constant power is delivered. A proportional integral derivative (PID) controller controls the amount of power by increasing the power level, and inherently the voltage level, until it reaches a set target valued. In one embodiment, the PID controller controls the amount of power by gradually increasing the power level. In a particularly advantageous embodiment, the PID controller controls the amount of power by rapidly increasing the power level. Further, to better control the ablation depth, the PID controller makes sure that the desired power level is achieved within a certain time window. In one embodiment, the generator is adapted to control the amount of energy delivered to the tissue over time based on the measured diameter of the esophagus. Furthermore, the generator can be adapted to normalize the density of energy delivered to the tissue over time based on the measured diameter of the esophagus so that equivalent energy densities (i.e., energy per unit are of electrode surface area $\{J/cm^2\}$) are delivered to esophagi of differing diameters. In another embodiment, the generator is adapted to control the amount of power delivered to the tissue over time based on the measured diameter of the esophagus so that equivalent power densities (i.e., power per unit area of electrode surface area $\{W/cm^2\}$) are delivered to esophagi of differing diameters.

In order to effectively ablate the mucosal lining of the esophagus, the system described herein controls the total energy delivered to the esophageal tissue and the amount of time for which the energy is delivered, as described above. Other methods may be similarly employed to ablate a desired surface area rapidly and circumferentially, while controlling the ablation depth. The generator 230 may be manually controlled by a user such that the amount of power density delivered to the esophageal tissue can be monitored over time. As such, the generator 230 is adapted to allow the user to select an appropriate power density to be delivered to the tissue in short burst. In one embodiment, the time for an effective treatment is less than one second. In another embodiment, the time is approximately 300 ms.

In order to effectively eliminate abnormal cells in the esophagus, energy must be applied such that a physiological change occurs at the cellular level within the esophagus lining. Methods of tracking the characteristics of the esophageal tissue and the changes in its cellular characteristics include monitoring the tissue impedance and/or the tissue temperature. The ablation time could be then adjusted based on the individual characteristics of the tissue and its measured impedance and/or temperature values.

Figure 19:
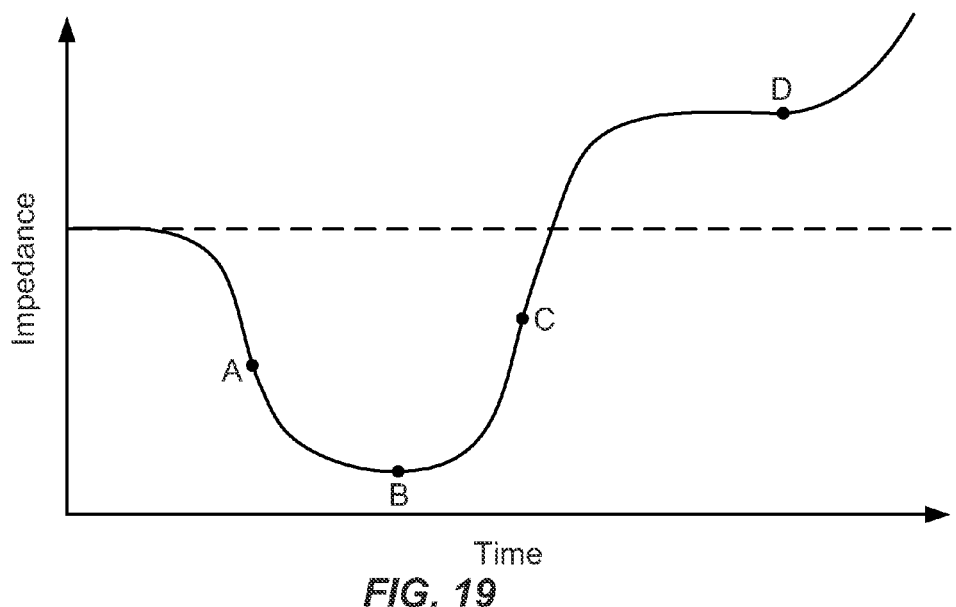
FIG. 19 illustrates a graphical representation of tissue impedance over time.

FIG. 19 illustrates a graphical representation of impedance measurements during ablation over time. During ablation, the tissue temperature rises, which causes a decrease in the tissue resistivity. This drop in impedance from an initial impedance value is represented by the exemplary reference points A and B. If the ablation continues beyond the reference point B, the tissue cell membranes rupture such that desiccation of cells occurs and resistivity of the tissue increases. The exemplary increased impedance value measured during this period of time is shown by reference point C. In order to control the depth of ablation and the extent of treatment in terms of the total volume of tissue desiccated, the generator 230 monitors the changes in the measured tissue impedance values. As such, the generator 230 delivers the energy to the tissue in a time window defined by the tissue impedance measurements. For example, in one embodiment, generator 230 may ablate only for the time it takes the tissue to reach an absolute impedance target. For example, the target targeted impedance value ranges from approximately 0.5-10 ohms. In another embodiment, generator 230 may ablate only until the impedance value decreases a pre-determined percentage from the initial impedance value of the tissue prior to ablation. Yet, in another embodiment, the time of ablation can depend on the point at which the impedance values reach an inflection point on the graph illustrated in FIG. 19, i.e., when the impedance values are between the reference points 13 and C. As such, the energy delivery could cease when the impedance reaches its minimum value, at which point it starts to increase. In another embodiment, the ablation time may be defined by the impedance value that exceeds a particular level. If the tissue impedance value reaches levels higher then the initial impedance value, as shown by the exemplary reference point D, the extent of the treatment may reach levels such that the esophageal wall is breached. As such, it may desirable to cease delivering energy to the tissue before the impedance reaches its initial value, e.g., reference value C.

Figure 20:
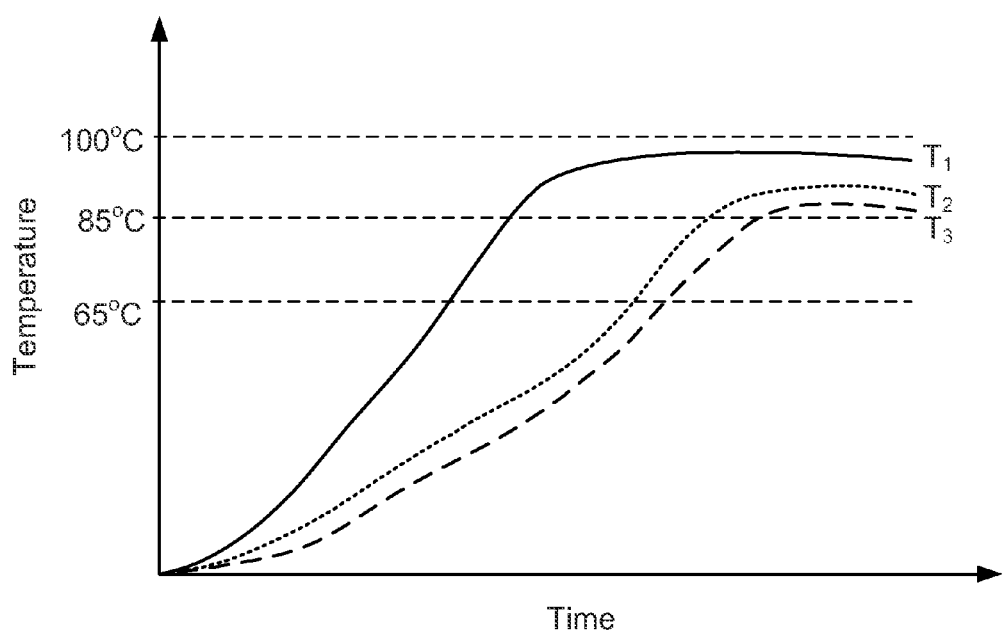
FIG. 20 illustrates a graphical representation of the tissue temperature over time.

FIG. 20 illustrates a graphical representation of the tissue temperature over time. When the tissue receives RF energy, heat is being generated. T1, T2 and T3 represent temperature curves of different sensors positioned at different locations within or outside the tissue to be ablated. For optimal ablation with controlled depth, the ablation time should be controlled such that the temperature of the tissue is less than 100° C. For example, if the desired ablation reaches inside the tissue approximately ½ to 1 millimeter from the surface, the generator 230 controls the ablation time such that the temperature of the tissue is between 65° C. and 95° C. Alternatively, the ablation time could be defined by the amount of time that it takes the tissue to heat to a preset target temperature. In this method, the generator 230 monitors the temperature of the tissue and, when the tissue has reached a certain temperature, generator 230 stops the delivery of the energy to the tissue.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. An apparatus for treating a tissue inside a body lumen, comprising:
   a treatment catheter having an expansion member, an electrode array on the expansion member, a pneumatic connector in communication with the interior of the expansion member and an electrical connection connected to the electrode array; and
   a generator comprising:
      an RF energy source and a generator electrical connector to attach to the electrical connection,
      a pump and a generator pneumatic connector to attach to the pneumatic connector;
      a mass-flow meter; and
      one or more pressure sensors, wherein
      the generator is configured to:
         determine a dimension of a distended body lumen utilizing one or more measurements from at least the mass-flow meter and the one or more pressure sensors; and
         inflate the expansion member and provide sufficient energy to the electrode array to sear the lining of the distended lumen based on the dimension of the distended body lumen determined by the generator.

2. An apparatus for treating a tissue inside a body lumen according to claim 1, wherein the generator is configured to inflate the treatment catheter to the same pressure used to inflate a sizing catheter utilized in determining the dimension of the distended body lumen.

3. An apparatus for treating a tissue inside a body lumen according to claim 1, wherein the generator is configured to provide the sufficient energy to the electrode array to sear the lining of the distended body lumen in less than 5 seconds.

4. An apparatus for treating a tissue inside a body lumen according to claim 3, wherein the generator is configured to provide the sufficient energy to the electrode array to produce an energy density of 1 J/cm2 to 50 J/cm2 to sear the lining of the distended body lumen.

5. An apparatus for treating a tissue inside a body lumen according to claim 2, wherein the generator is configured to inflate the sizing catheter to distend the body lumen with a pressure of between about 1 psig and about 10 psig.

6. An apparatus for treating a tissue inside a body lumen according to claim 2, wherein after connecting and inflating the sizing catheter, the generator is configured to display a recommended treatment catheter size.

7. An apparatus for treating a tissue inside a body lumen according to claim 1, wherein the generator is configured to provide the sufficient energy to the electrode array for sear the lining of the distended lumen by delivering energy to different circumferential sections of the distended lumen wall sequentially in less than 5 seconds.

8. An apparatus for treating a tissue inside a body lumen according to claim 2, wherein the generator is further configured to inflate the sizing catheter to unfold the walls of the body lumen.

9. An apparatus for treating a tissue inside a body lumen according to claim 1, wherein the generator is further configured to inflate the expansion member to unfold the walls of the body lumen while providing the sufficient energy to the electrode array to sear the lining of the distended lumen.

10. An apparatus for treating a tissue inside a body lumen according to claim 1, wherein the generator is configured to deliver the sufficient energy to the electrode array for treatment of Barrett's esophagus.

* * * * *